(12) United States Patent
Kawamura et al.

(10) Patent No.: US 12,201,691 B2
(45) Date of Patent: Jan. 21, 2025

(54) CORE-SHELL STRUCTURE, PREPARATION, MEDICINE FOR EXTERNAL APPLICATION, TAPE AGENT AND COSMETIC PRODUCT

(71) Applicant: SEKISUI CHEMICAL CO., LTD., Osaka (JP)

(72) Inventors: Daichi Kawamura, Osaka (JP); Takayuki Akamine, Osaka (JP); Saori Tone, Osaka (JP); Yuuta Nakamura, Osaka (JP); Izumi Matsumoto, Osaka (JP); Kazushi Itou, Osaka (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 494 days.

(21) Appl. No.: 16/990,634

(22) Filed: Aug. 11, 2020

(65) Prior Publication Data

US 2020/0368356 A1 Nov. 26, 2020

Related U.S. Application Data

(62) Division of application No. 16/089,309, filed as application No. PCT/JP2018/004232 on Feb. 7, 2018, now abandoned.

(30) Foreign Application Priority Data

Feb. 9, 2017 (JP) ................. 2017-022175
Jun. 1, 2017 (JP) ................. 2017-109314
Sep. 25, 2017 (JP) ................. 2017-183328

(51) Int. Cl.
| | | |
|---|---|---|
| A61K 47/14 | (2017.01) | |
| A61K 8/37 | (2006.01) | |
| A61K 8/42 | (2006.01) | |
| A61K 9/00 | (2006.01) | |
| A61K 9/06 | (2006.01) | |
| A61K 9/10 | (2006.01) | |
| A61K 9/70 | (2006.01) | |
| A61K 47/18 | (2017.01) | |
| A61K 47/26 | (2006.01) | |
| A61Q 19/00 | (2006.01) | |

(52) U.S. Cl.
CPC ............... *A61K 47/14* (2013.01); *A61K 8/37* (2013.01); *A61K 8/42* (2013.01); *A61K 9/0092* (2013.01); *A61K 9/06* (2013.01); *A61K 9/10* (2013.01); *A61K 9/70* (2013.01); *A61K 47/18* (2013.01); *A61K 47/26* (2013.01); *A61Q 19/00* (2013.01); *A61K 9/0031* (2013.01); *A61K 9/0043* (2013.01)

(58) Field of Classification Search
None
See application file for complete search history.

(56) References Cited

U.S. PATENT DOCUMENTS

| | | | |
|---|---|---|---|
| 2007/0243132 A1 | 10/2007 | Russell-Jones et al. | |
| 2009/0238846 A1* | 9/2009 | Fujii | A61K 31/196 514/567 |
| 2012/0207794 A1* | 8/2012 | Goto | A61K 9/5089 424/400 |
| 2012/0264742 A1* | 10/2012 | Furuishi | A61P 25/04 514/777 |
| 2013/0059764 A1 | 3/2013 | Tashiro et al. | |
| 2017/0014417 A1 | 1/2017 | Lipp | |
| 2017/0232106 A1* | 8/2017 | Akamine | A61K 31/47 514/89 |
| 2018/0185273 A1 | 7/2018 | Akamine et al. | |
| 2019/0117777 A1 | 4/2019 | Kawamura et al. | |
| 2020/0368356 A1 | 11/2020 | Kawamura et al. | |

FOREIGN PATENT DOCUMENTS

| | | |
|---|---|---|
| EP | 2 570 112 A1 | 3/2013 |
| JP | 2011-241156 A | 12/2011 |
| JP | 4843494 B2 | 12/2011 |
| JP | 5531230 B2 | 6/2014 |
| JP | 2016-60725 A | 4/2016 |
| JP | 2016-179962 A | 10/2016 |
| JP | 2016-179963 A | 10/2016 |
| JP | 2017-14128 A | 1/2017 |
| JP | 2017-14130 A | 1/2017 |
| JP | 6370520 B1 | 8/2018 |
| JP | 6386691 B1 | 9/2018 |
| RU | 2 554 814 C2 | 6/2015 |
| WO | WO-2006/025583 A1 | 3/2006 |
| WO | WO-2010/075465 A1 | 7/2010 |

(Continued)

OTHER PUBLICATIONS

Cornwell et al.; "Glyceryl monocaprylate/caprate as a moderate skin permeation enhancer," 1998, Elsevier; International Journal of Pharmaceutics, vol. 171, pp. 243-255. (Year: 1998).*
Okumura et al.; "Effect of monoglycerides on the percutaneous absorption of papaverine hydrochloride," 1990, Drug design and delivery vol. 6, No. 2, pp. 137-148. (Year: 1990).*
Lara et al.; "In vitro drug release mechanism and drug loading studies of cubic phase gels," 2005, Elsevier, International Journal of Pharmaceutics, vol. 293, pp. 241-250. (Year: 2005).*
Salve et al.; "Formulation and Evaluation of Solid Lipid Nanoparticle Based Transdermal Drug Delivery System for Alzheimer's Disease," Research Journal of Pharmaceutical Dosage Forms and Technology. 8(2): Apr.-Jun. 2016, pp. 73-80. (Year: 2016).*
Cornwell, Paul A. et al., "Glyceryl monocaprylate/caprate as a moderate skin penetration enhancer," International Journal of Pharmaceutics, 1998, vol. 171, pp. 243-255.

(Continued)

*Primary Examiner* — Tigabu Kassa
*Assistant Examiner* — Ivan A Greene
(74) *Attorney, Agent, or Firm* — Cheng Law Group, PLLC

(57) ABSTRACT

Provided is a core-shell structure having an excellent immediate effect in transdermal absorption of an active ingredient. A core-shell structure comprising a core portion containing an active ingredient, and a shell portion containing a surfactant having an HLB value of 4 to 14, the core portion being solid, and the surfactant containing a saturated hydrocarbon group having 7 to 15 carbon atoms or an unsaturated hydrocarbon group having 7 to 17 carbon atoms.

7 Claims, 3 Drawing Sheets

(56) References Cited

FOREIGN PATENT DOCUMENTS

| WO | WO-2016043323 A1 * | 3/2016 | ............. A61K 31/13 |
|---|---|---|---|
| WO | WO-2017/002865 A1 | 1/2017 | |

OTHER PUBLICATIONS

Goto, Masahiro et al., "Development of New Surfactant For Liquid Surfactant Membrane Process", Journal of Chemical Engineering of Japan, 1987, vol. 20, No. 2, pp. 157-164.
Kamiya, Noriho et al., "Catalytic and Structural Properties of Surfactant-Horseradish Peroxidase Complex in Organic Media", Biotechnology Progress, 2000, vol. 16, pp. 52-58.
Kitaoka, Momoko et al., "Solid-in-oil nanodispersions for transdermal drug delivery systems", Biotechnology Journal, 2016, vol. 11, pp. 1375-1385.
The Merck Index™ Online (entry for vardenafil; p. 1, last revised 2013; © Royal Society of Chemistry), retrieved from <https://www.rsc.org/Merck-Index/monograph/> on Sep. 28, 2019. (Year: 2013).
Neyts, Johan et al., "Hydrogels Containing Monocaprin Prevent Intravaginal and Intracutaneous Infections With HSV-2 in Mice: Impact on the Search for Vaginal Microbiocides," Journal of Medical Virology, 2000, vol. 61, pp. 107-110.
Okada, Masahide et al., "HLB of surfactant—physical and chemical meaning thereof and novel calculation method—", Oil Recovery Study, 1958, vol. 7, No. 7, pp. 434-438.
Okumura, Mutsuo et al., "Effect of monoglycerides on the percutaneous absorption of papaverine hydrochloride," Drug Design and Delivery, 1990, vol. 6, pp. 137-148.
Supplementary European Search Report for the Application No. EP 18 751 519.2 dated Feb. 3, 2020.
The First Office Action for the Application No. 201880002393.6 from The State Intellectual Property Office of the People's Republic of China dated Sep. 10, 2019.
International Search Report for the Application No. PCT/JP2018/004232 mailed Mar. 20, 2018.
Written Opinion of the International Searching Authority (PCT/ISA/237) for Application No. PCT/JP2018/004232 mailed Mar. 20, 2018 (English Translation mailed Aug. 22, 2019).
Russian Office Action for Application No. 2019127198/04(053323) dated Dec. 18, 2020.
Taiwanese Office Action for the Application No. 107104735 dated Jun. 15, 2021.
Notification of Reasons for Refusal for the Application No. 2018-149074 from Japan Patent Office mailed Nov. 2, 2021.
Australian Examination Report No. 1 for the Application No. 2018218868 dated Mar. 8, 2023.

* cited by examiner

[FIG. 1]
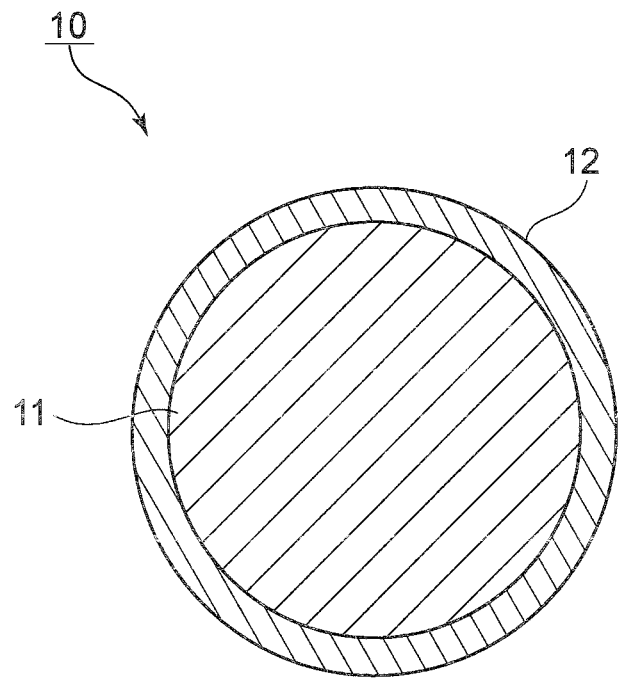
[FIG. 2]
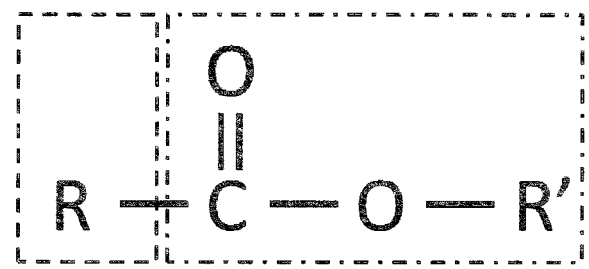
[FIG. 3]
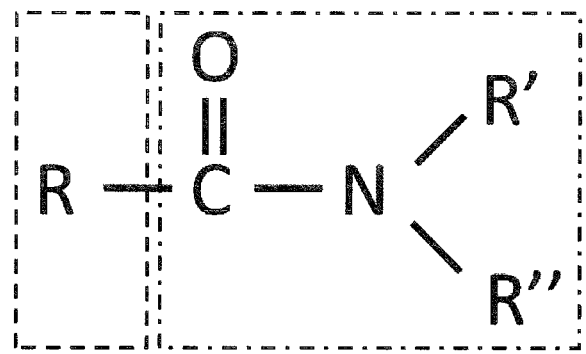

[FIG. 4]
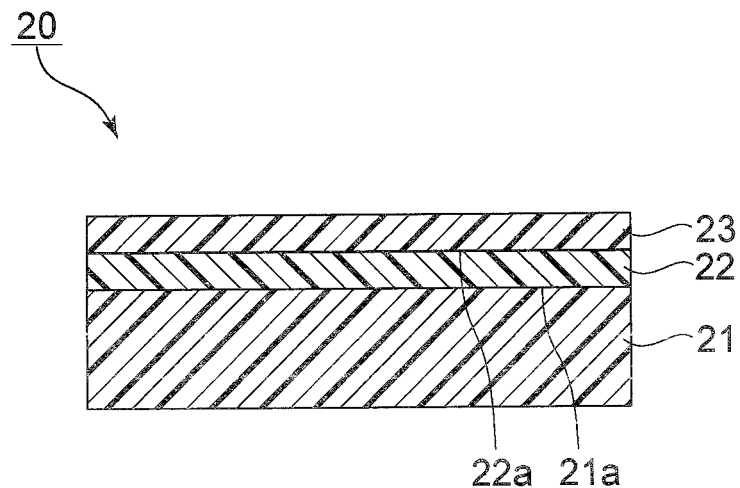
[FIG. 5]
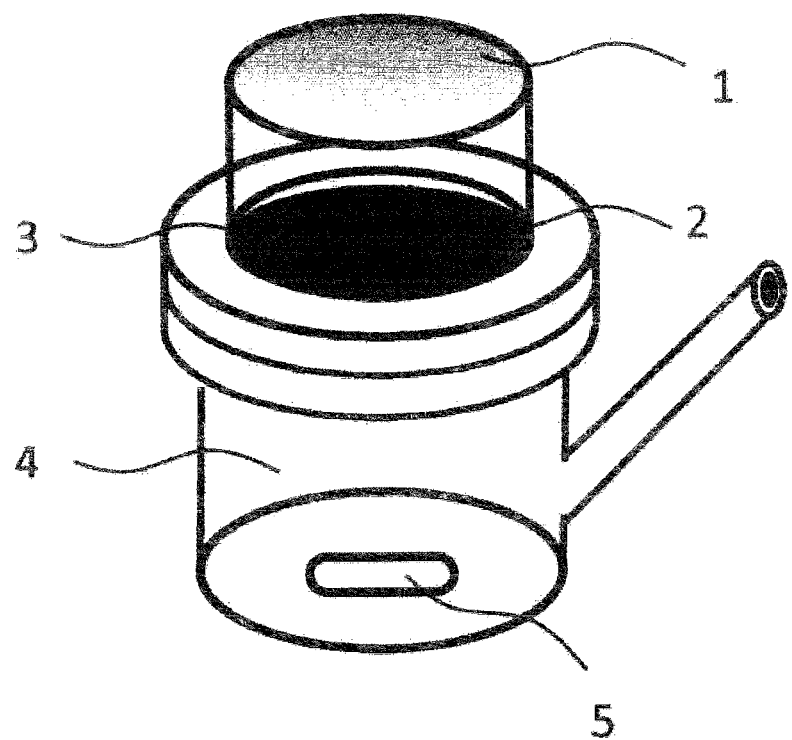

[FIG. 6]
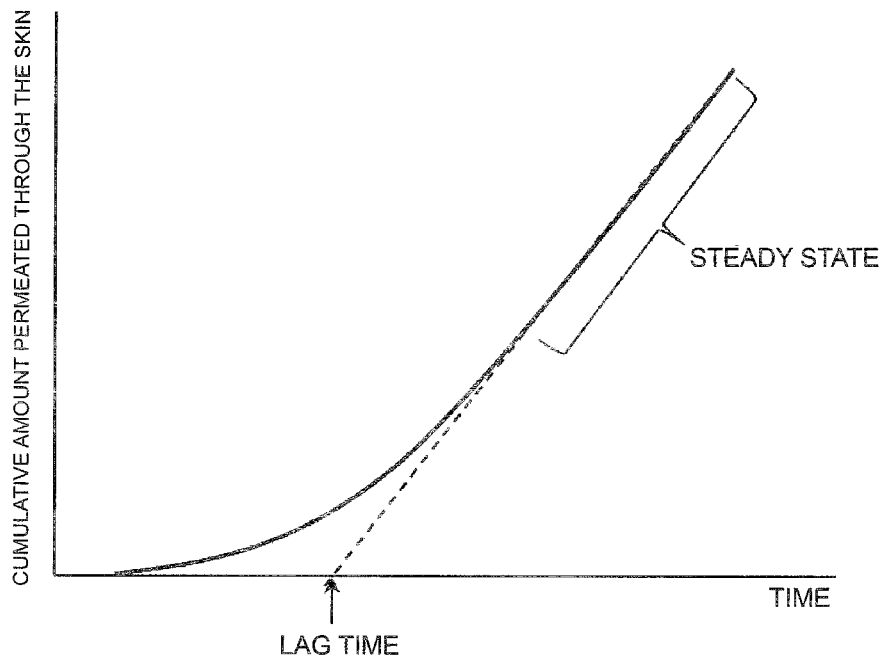
[FIG. 7]
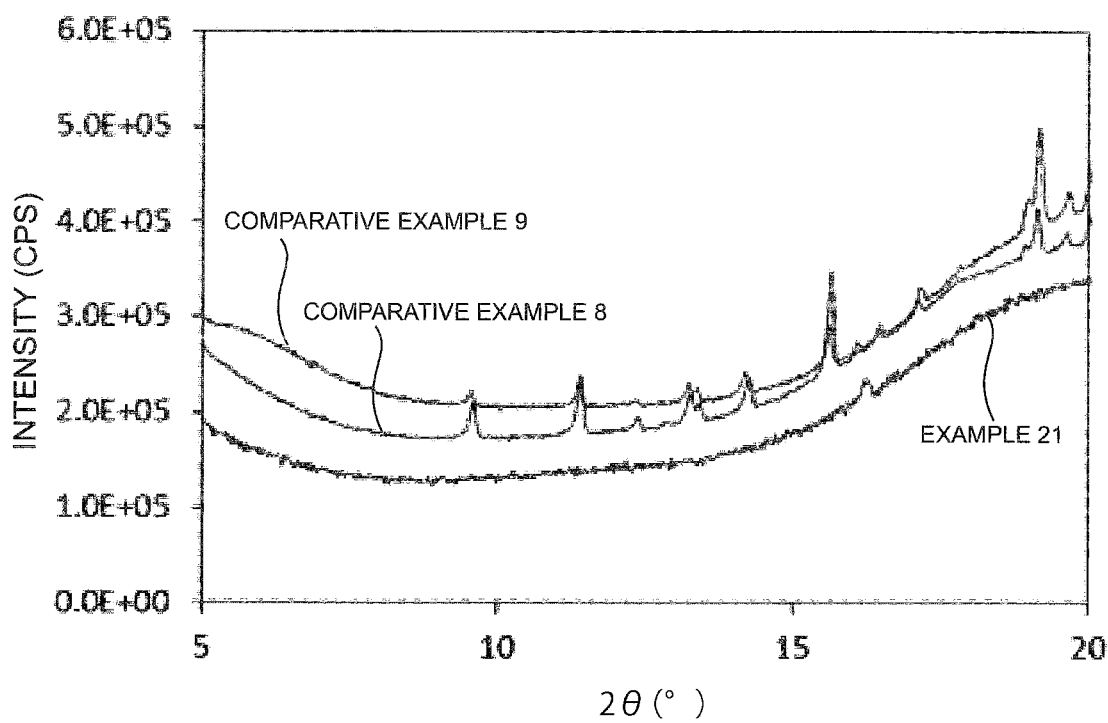

CORE-SHELL STRUCTURE, PREPARATION, MEDICINE FOR EXTERNAL APPLICATION, TAPE AGENT AND COSMETIC PRODUCT

CROSS-REFERENCE TO RELATED APPLICATIONS

This application is a Divisional Applications of patent application Ser. No. 16/089,309, filed on Sep. 27, 2018, which is a 371 application of Application Serial No. PCT/JP2018/004232, filed on Feb. 7, 2018, which is based on Japanese Patent Application Nos. 2017-022175 filed on Feb. 9, 2017 and 2017-109314 filed Jun. 1, 2017 and 2017-183328 filed on Sep. 25, 2017, the entire contents of which are hereby incorporated by reference.

TECHNICAL FIELD

The present invention relates to a core-shell structure, and a formulation, an external medicine, a tape preparation, and a cosmetic including the core-shell structure.

BACKGROUND ART

In the fields of external medicines, cosmetics, and the like, techniques for transdermal absorption of an active ingredient such as drugs have been developed. Processes for transdermal absorption of an active ingredient may be influenced by skin barrier function, metabolism or the like, and such influence is known to depend on drugs.

Patent Literature 1 described below reports that a formulation including an active ingredient and sucrose erucic acid ester has increased the amount of the active ingredient transdermally absorbed.

Patent Literature 2 described below reports that a formulation including an active ingredient and a surfactant such as tetraglycerin-condensed ricinoleate has increased the amount transdermal absorption.

CITATION LIST

Patent Literature

Patent Literature 1: Japanese Patent No. 4843494
Patent Literature 2: Japanese Patent No. 5531230

SUMMARY OF INVENTION

Technical Problem

When the formulation of Patent Literatures 1 or 2 for an external medicine or cosmetic is used, however, the transdermal absorbability of the active ingredient has not yet been sufficient. The formulations of Patent Literatures 1 and 2, in particular, have a long transdermal absorption delay time for the active ingredient (lag time: time required for an active ingredient to permeate the skin), and a long time may have been required from the administration to the generation of the medicinal effect. In other words, the formulations of Patent Literatures 1 and 2 have provided an insufficient immediate effect in transdermal absorption of the active ingredient.

It is an object of the present invention to provide a core-shell structure, a formulation, an external medicine, a tape preparation, and a cosmetic that have an excellent immediate effect in transdermal absorption of an active ingredient.

Solution to Problem

The present inventors have intensively studied to solve the above problem, and as a result, have found that the above problem can be solved by using a core-shell structure that includes a core portion containing an active ingredient and a shell portion containing a surfactant having an HLB value of 4 to 14, the core portion being solid, and the surfactant containing a saturated hydrocarbon group having 7 to 15 carbon atoms or an unsaturated hydrocarbon group having 7 to 17 carbon atoms. The present invention has been accomplished through further attempts made on the basis of this finding, and embraces the following aspects.

That is to say, a core-shell structure according to the present invention includes a core portion containing an active ingredient and a shell portion containing a surfactant having an HLB value of 4 to 14, wherein the core portion is solid, and the surfactant has a saturated hydrocarbon group having 7 to 15 carbon atoms or an unsaturated hydrocarbon group having 7 to 17 carbon atoms.

In a specific aspect of the core-shell structure according to the present invention, the surfactant is a surfactant formed by linking an alcohol with a fatty acid via ester bonding or amide bonding, the alcohol has a molecular weight in the range of 70 g/mol to 330 g/mol.

In another specific aspect of the core-shell structure according to the present invention, the surfactant contains at least one selected from the group consisting of sorbitan fatty acid esters, glycerin fatty acid esters, propylene glycol fatty acid esters, and fatty acid alkanolamides. Preferably, the surfactant contains at least one selected from the group consisting of sorbitan fatty acid esters, glycerin fatty acid esters, and propylene glycol fatty acid esters.

In another specific aspect of the core-shell structure according to the present invention, the glycerin fatty acid ester is at least one selected from monoglycerin fatty acid esters, diglycerin fatty acid esters, and triglycerin fatty acid esters.

In still another aspect of the core-shell structure according to the present invention, the mass ratio between the active ingredient and the surfactant (active ingredient:surfactant) is 1:0.5 to 1:100.

In still another aspect of the core-shell structure according to the present invention, the mass ratio between the active ingredient and the surfactant (active ingredient:surfactant) is 1:5 to 1:100.

In still another aspect of the core-shell structure according to the present invention, the mass ratio between the active ingredient and the surfactant (active ingredient:surfactant) is 1:0.5 to 1:5.

In still another aspect of the core-shell structure according to the present invention, the mass ratio between the active ingredient and the surfactant (active ingredient:surfactant) is 1:0.5 to 1:2.

A formulation according to the present invention contains a core-shell structure constituted according to the present invention.

An external medicine according to the present invention contains a core-shell structure constituted according to the present invention.

A tape preparation according to the present invention contains a core-shell structure constituted according to the present invention.

A cosmetic according to the present invention contains a core-shell structure constituted according to the present invention.

Advantageous Effects of Invention

According to the present invention, it is possible to provide a core-shell structure, a formulation, an external medicine, a tape preparation, and a cosmetic that have an excellent immediate effect in transdermal absorption of active ingredients. When the surfactant contains at least one selected from the group consisting of sorbitan fatty acid esters, glycerin fatty acid esters, and propylene glycol fatty acid esters, it is possible to provide a core-shell structure, a formulation, an external medicine, a tape preparation, and a cosmetic that have an excellent immediate effect in transdermal absorption and additionally have further reduced skin irritation.

BRIEF DESCRIPTION OF DRAWINGS

FIG. 1 is a schematic cross-sectional view of a core-shell structure according to one embodiment of the present invention.

FIG. 2 is a view for illustrating the hydrophilic moiety and the hydrophobic moiety of a surfactant formed by an alcohol and a fatty acid linked via ester bonding.

FIG. 3 is a view used for illustrating the hydrophilic moiety and the hydrophobic moiety of a surfactant formed by an alcohol and a fatty acid linked via amide bonding.

FIG. 4 is a schematic cross-sectional view showing a tape preparation according to one embodiment of the present invention.

FIG. 5 is a simplified view of a drug skin permeation test cell used in Test Example 1.

FIG. 6 is a schematic view used for illustrating a lag-time measurement method.

FIG. 7 shows X-ray diffraction spectra of the tape preparations obtained in Example 21, Comparative Example 8, and Comparative Example 9.

DESCRIPTION OF EMBODIMENTS

The details of the present invention will be described hereinafter.
[Core-Shell Structure]

A core-shell structure according to the present invention includes a core portion containing an active ingredient and a shell portion containing a surfactant.

In the present invention, the core portion and the shell portion may bind to each other by intermolecular force or the like to form an assembly. However, from the viewpoint of further enhancing the transdermal absorbability of the active ingredient, at least a portion of the surface of the core portion is preferably coated with the shell portion.

More specifically, 30% or more of the surface of the core portion is preferably coated with the shell portion. More preferably 50% or more, still more preferably 70% or more, even more preferably 85% or more, particularly preferably 95% or more, and most preferably 99% or more of the surface is coated. The surface of the core portion may be completely coated with the shell portion. The core-shell structure, which is configured as described above, can release the active ingredient contained in the core portion inside the body when applied onto the skin, for example.

In the present invention, the above core portion is solid. Since the core portion is solid, the stability in a base described below can be further enhanced. In this case, dispersing the core-shell structure in a base phase as an oil phase can form a formulation having an S/O (Solid in Oil) type structure.

As described in the section of a production method below, the core-shell structure of the present invention can be obtained by drying a W/O emulsion to remove the solvent (aqueous solvent and oil solvent), and thus, its core portion is solid (S in the S/O (Solid in Oil) type described above). The step of drying the W/O emulsion preferably removes the moisture substantially completely. Specifically, the water content is preferably 5% by weight or less, more preferably 2% by weight or less, still more preferably 1% by weight or less, particularly preferably 0.5% by weight or less, according to measurement by the Karl fisher method, for example. Thus, the core-shell structure of the present invention is different from a W/O emulsion.

In the present invention, the surfactant contained in the shell portion has an HLB value of 4 to 14. The surfactant includes a saturated hydrocarbon group having 7 to 15 carbon atoms or an unsaturated hydrocarbon group having 7 to 17 carbon atoms. Note that, "aa to bb" herein refers to "aa or more and bb or less". For example, an HLB value of 4 to 14 is intended to refer to an HLB value of 4 or more and 14 or less.

The core-shell structure of the present invention has an excellent immediate effect in transdermal absorption of an active ingredient because the HLB value of the surfactant contained in the shell portion is in a specific range and additionally the number of carbon atoms in the hydrocarbon group of the surfactant is in the specific range described above.

The reason for this can be explained as follows. When the HLB value of the surfactant contained in the shell portion is in the specific range described above, it is possible to reduce the barrier function of the skin, and thus, to obtain a core-shell structure having an excellent immediate effect in transdermal absorption.

When the number of carbon atoms in the hydrocarbon group of the surfactant is in the specific range described above, the releasability of the active ingredient from particles in the body increases. Accordingly, it is possible to obtain a core-shell structure having an excellent immediate effect in transdermal absorption.

The core-shell structure of the present invention, which has an excellent immediate effect in transdermal absorption of active ingredients, can be suitably used for formulations. Among others, the core-shell structure can be suitably used in the fields of external medicines, tape preparations, cosmetics, injections or the like.

One example of the core-shell structure of the present invention will be now described with reference to the drawing.

FIG. 1 is a schematic cross-sectional view of a core-shell structure according to one embodiment of the present invention.

As shown in FIG. 1, a core-shell structure 10 includes a core portion 11 and a shell portion 12. The surface of the core portion 11 is coated with the shell portion 12.

The shape of the core-shell structure of the present invention is not limited to such spherical particles. The core-shell structure of the present invention may be a particle having a rod-like, cubic, lens-like, micellar, lamellar, hexagonal, bicellar, sponge-like or echino shape or may be amorphous. As described above, the shape of the core-shell structure of the present invention is not particularly limited. As described above, at least a portion of the surface of the core portion is preferably coated with the shell portion.

The size of the core-shell structure of the present invention is not particularly limited. From the viewpoint of further enhancing the transdermal absorbability of the active ingredient, the average size of the core-shell structure can be preferably 1 nm to 100 μm.

Note that, in the present invention, the average size of the core-shell structure is the number average diameter calculated by the dynamic light scattering method in the case of dispersion in a solvent (e.g., squalane or the like).

The details of the core portion and shell portion will be now described.

(Core Portion)

The core portion contains at least an active ingredient.

Specific examples of the active ingredient include, but are not particularly limited to, dementia therapeutic agents, antiepileptic agents, antidepressants, antiparkinsonian agents, anti-allergic agents, anticancer agents, antidiabetics, antihypertensive agents, respiratory disease drugs, erectile dysfunction drugs, skin disease therapeutic agents, and local analgesics. One active ingredient may be used singly or two or more active ingredients may be used in combination.

More specific examples include memantine, donepezil, diphenhydramine, vardenafil, octreotide, rivastigmine, galanthamine, nitroglycerin, lidocaine, fentanyl, male hormones, female hormones, nicotine, clomipramine, nalfurafine, metoprolol, fesoterodine, tandospirone, beraprost sodium, taltirelin, lurasidone, nefazodone, rifaximin, benidipine, doxazosin, nicardipine, formoterol, lomerizine, amlodipine, teriparatide, bucladesine, cromoglicic acid, lixisenatide, exenatide, liraglutide, lanreotide, glucagon, oxytocin, calcitonin, elcatonin, glatiramer, risedronic acid, diclofenac, and ascorbic acid and pharmaceutically acceptable salts thereof.

The pharmaceutically acceptable salt is not particularly limited, and any of acid salts and basic salts can be employed. Examples of the acid salts include inorganic acid salts such as hydrochloride, hydrobromide, sulfate, nitrate, and phosphate, and organic acid salts such as acetate, propionate, tartrate, fumarate, maleate, malate, citrate, methanesulfonate, bensenesulfonate, and p-toluenesulfonate. Examples of the basic salts include alkali metals salts such as sodium salts and potassium salts, and alkaline-earth metal salts such as calcium salts and magnesium salts. Specific examples of active ingredient salts include memantine hydrochloride, donepezil hydrochloride, rivastigmine tartrate, galanthamine hydrobromide, clomipramine hydrochloride, diphenhydramine hydrochloride, nalfurafine hydrochloride, metoprolol tartrate, fesoterodine fumarate, vardenafil hydrochloride hydrate, nalfurafine hydrochloride, tandospirone citrate, beraprost sodium, lurasidone hydrochloride, nefazodone hydrochloride, benidipine hydrochloride, doxazosin mesilate, nicardipine hydrochloride, formoterol fumarate, lomerizine hydrochloride, and amlodipine besilate.

An active ingredient to be formulated into a cosmetic is not particularly limited, so long as it is required to penetrate transdermally. Examples of the active ingredients include vitamin ingredients such as vitamin C and vitamin E, moisturizing ingredients such as hyaluronic acid, ceramide, and collagen, skin-whitening ingredients such as tranexamic acid and arbutin, hair growth ingredients such as minoxidil, beauty ingredients such as FGF (fibroblast growth factor) and EGF (epidermal growth factor), and salts or derivatives thereof.

The active ingredient in the present invention preferably has low skin irritation. Low skin irritation means having a primary irritation index (P.I.I.) of 5 or less. Note that, the primary irritation index can be measured by a method described below.

1. Preparation of Formulation

An active ingredient is added to an ointment base Plastibase (manufactured by Taisho Pharmaceutical Co., Ltd.) such that its content reaches 4% by weight based on the total weight, mixed, and dispersed therein to produce a formulation.

2. Skin Irritation Evaluation (Evaluation of Primary Irritation Index)

The dorsal skin of a rabbit is shaved with an electric clipper (with an electric shaver as required). Healthy skin at two points on either side of the dorsal mid-line of the dorsal skin, that is, at four points in total, is used as administration sites. Next, the formulation prepared is taken with a spatula and spread evenly on pieces of lint each having a size of 2 cm×2 cm, and the pieces are attached onto the administration sites. The lint pieces are fixed by covering with a non-woven adhesive bandage (manufactured by Nichiban Co., Ltd., MESHPORE, No. 50). Then, the administration sites are altogether wrapped with gauze and then sealed by covering with an adhesive cloth elastic bandage (manufactured by Nichiban Co., Ltd., ELASTPORE, No. 100). The sealing is terminated 24 hours after the start of the administration, and the administration specimens are removed.

Skin reaction at 24 hours after the administration (30 minutes after the sealing is terminated and the administration specimens are removed) is observed by the naked eye. Thereafter, skin reaction further at 48 hours and 72 hours after the administration (30 minutes after the sealing is terminated and the administration specimens are removed) is observed by the naked eye in the same manner. Skin reaction evaluation is intended to be carried out based on the Draize scoring shown in Table 1 below.

TABLE 1

| Degree of skin reaction | Score |
| --- | --- |
| Erythema and eschar formation | |
| No erythema | 0 |
| Very slight erythema (barely perceptible) | 1 |
| Slight erythema | 2 |
| Moderate to severe erythema | 3 |
| Crimson severe erythema and slight eschar formation (injuries in depth) | 4 |
| Edema formation | |
| No edema | 0 |
| Very slight edema (barely perceptible) | 1 |
| Slight edema (Well defined) | 2 |
| Moderate edema (raised approximately 1 mm) | 3 |
| Severe edema (raised more than 1 mm and extending to the periphery) | 4 |

Specifically, individual skin reaction scores (sum of erythema and eschar formation and edema formation) at the administration sites of each rabbit are calculated for each administration specimen at each observation time. Thereafter, the primary irritation index (primary irritation index; P.I.I.) is calculated from the individual scores each at 24 hours and 72 hours after the administration (the score at 48 hours after the administration is not added). Specifically, the following equations (1) and (2) are used for the calculation.

$$\text{Average score of each administration site} = (\text{Sum of individual scores at 24 hours and 72 hours after the administration})/2 \quad \text{Equation (1)}$$

$$\text{Primary irritation index (P.I.I.)} = (\text{Sum of the average score of each administration site})/(3(\text{rabbits})) \quad \text{Equation (2)}$$

The primary irritation index measured by the method described above is preferably 2 or less, more preferably 1 or less.

Examples of low skin-irritant active ingredients include loxoprofen sodium dihydrate (P.I.I.=0.3), rivastigmine (P.I.I.=0.5), donepezil (P.I.I.=0.5), and memantine hydrochloride (P.I.I.=2.5).

Such an active ingredient is preferably hydrophilic. When the active ingredient is a hydrophilic drug, a drug required to have a systemic effect or local effect is usually used.

The active ingredients, if easily transdermally absorbed, are preferable. The active ingredients are preferably, but are not particularly limited to, compounds exhibiting an octanol/water partition coefficient of −2 to 6. In this case, the skin permeability of the active ingredient is further enhanced. From the viewpoint of further enhancing the skin permeability of the active ingredient, the octanol/water partition coefficient is preferably −1 or more, more preferably 0 or more. The octanol/water partition coefficient of the active ingredient is also preferably 4 or less, more preferably 1 or less. When the octanol/water partition coefficient of the active ingredient is equal to or less than the upper limit described above, the skin permeability of the active ingredient is further enhanced.

Note that, in the present invention, the octanol/water partition coefficient is determined based on active ingredient concentration of each phase obtained by adding an active ingredient to a flask containing octanol and an aqueous buffer of pH 7, shaking the flask, and then determining the concentration. Specifically, the partition coefficient can be determined by calculation using an equation: Octanol/water partition coefficient=$\log_{10}$(concentration in an octanol phase/concentration in an aqueous phase).

An amount of the active ingredient contained in the core-shell structure, although depending on the type of the active ingredient, is, for example, preferably 1% by weight to 70% by weight, more preferably 5% by weight to 70% by weight as a raw material weight. The raw material weight is a value obtained on the basis of the total weight of all the raw materials contained in the core-shell structure.

The core portion may contain two or more active ingredients as active ingredients as required.

The molecular weight of the active ingredient is not particularly limited. The molecular weight of the active ingredient is preferably 250 g/mol or more, more preferably 300 g/mol or more, preferably 7500 g/mol or less, more preferably 6500 g/mol or less, still more preferably 1500 g/mol or less.

(Shell Portion)

The shell portion contains a surfactant having an HLB value of at least 4 to 14. The shell portion also contains a surfactant of which hydrocarbon group is a saturated hydrocarbon having 7 to 15 carbon atoms or an unsaturated hydrocarbon having 7 to 17 carbon atoms. The shell portion preferably contains a surfactant of which hydrophilic moiety has a molecular weight of 100 g/mol to 350 g/mol. The molecular weight of the hydrophilic moiety of the surfactant is not particularly limited.

An HLB (abbreviation of Hydrophile Lypophile Balance) value in the present invention, which is an index showing that an emulsifier is hydrophilic or lipophilic, takes a value of 0 to 20. A smaller HLB value indicates a higher lipophilicity.

In the present invention, the HLB value is calculated by the following Griffin equation.

HLB value=20×[(Molecular weight of hydrophilic moiety)/(Total molecular weight)]

A weighted average of the HLB value can be calculated using the following calculation equation.

A calculation equation for a weighted average value when surfactants having HLB values of A, B, and C are used in weights of x, y, and z, respectively, is as follows:

$(xA+yB+zC)/(x+y+z)$.

When a surfactant contains a plurality of hydrocarbon groups, the hydrocarbon group of which content in the surfactant is the highest is taken as the hydrocarbon group of the surfactant of the present invention.

Particularly when a surfactant contains a plurality of hydrocarbon groups having different number of carbon atoms, the number of carbon atoms in the hydrocarbon group of which content in the surfactant is the highest is taken as the number of carbon atoms in the hydrocarbon group of the surfactant of the present invention.

For example, specifically, when a surfactant is coconut oil fatty acid ester, the surfactant contains a saturated hydrocarbon group having 11 carbon atoms in the largest amount. Thus, the hydrocarbon group of coconut oil fatty acid ester is a saturated hydrocarbon group, and the number of carbon atoms in the hydrocarbon group is 11.

When a plurality of surfactants is contained, the number of carbon atoms in the hydrocarbon group of which content in the plurality of surfactants is the highest is taken as the number of carbon atoms in the hydrocarbon group in the surfactant of the present invention.

The HLB value of the surfactant or, when a plurality of surfactants is contained, the weighted average value of the HLB value is 4 or more and 14 or less, more preferably 5 or more and 12 or less.

The surfactant may have at least one of a saturated hydrocarbon group such as an alkyl group and an unsaturated hydrocarbon group such as alkenyl group or alkynyl group.

The number of carbon atoms in the saturated hydrocarbon group is 7 or more and 15 or less, preferably 7 or more and 11 or less. When the number of carbon atoms in the saturated hydrocarbon group is equal to or more than the lower limit described above, the coatability of the surface of the core portion with the shell portion will be further enhanced. Accordingly, it is possible to obtain a core-shell structure having a further more excellent immediate effect in transdermal absorption. When the number of carbon atoms in the saturated hydrocarbon group is equal to or less than the upper limit described above, the releasability of the active ingredient from the core-shell structure in the body is further enhanced, and thus, it is possible to obtain a core-shell structure having a further more excellent immediate effect in transdermal absorption.

The number of carbon atoms in the unsaturated hydrocarbon group is 7 or more and 17 or less, preferably 7 or more and 13 or less, more preferably 7 or more and 11 or less. When the number of carbon atoms in the unsaturated hydrocarbon group is equal to or more than the lower limit described above, the coatability of the surface of the core portion with the shell portion will be further enhanced. Accordingly, it is possible to obtain a core-shell structure having a further more excellent immediate effect in transdermal absorption. When the number of carbon atoms in the unsaturated hydrocarbon group is equal to or less than the upper limit described above, the releasability of the active ingredient from the core-shell structure in the body is further enhanced, and thus, it is possible to obtain a core-shell structure having a further more excellent immediate effect in transdermal absorption.

The molecular weight of the hydrophilic moiety of the surfactant is preferably 100 g/mol or more and 350 g/mol or less, more preferably 100 g/mol or more and 300 g/mol or less, still more preferably 100 g/mol or more and 200 g/mol or less. When the molecular weight of the hydrophilic moiety of the surfactant is equal to or more than the lower limit described above, the coatability of the core portion with the shell portion will be further enhanced. Accordingly, it is possible to obtain a core-shell structure having a further enhanced immediate effect in transdermal absorption. When the molecular weight of the hydrophilic moiety of the surfactant is equal to or less than the upper limit described above, the releasability of the active ingredient from particles in the body further increases. Accordingly, it is possible to obtain a core-shell structure having a further enhanced immediate effect in transdermal absorption.

Note that, the hydrophilic moiety of a surfactant refers to the portion remaining after the hydrocarbon group of the constituent fatty acid is removed from the entire surfactant molecule. For example, in the case of sorbitan monooleate, the molecular weight of the hydrophilic moiety is calculated to be 191.2 g/mol by subtracting the molecular weight of the hydrocarbon group of constituent fatty acid from the molecular weight of the entire surfactant molecule, because the molecular weight of the total surfactant molecule is 428.6 g/mol and the molecular weight of the hydrocarbon group of monooleic acid as the constituent fatty acid is 237.4 g/mol.

The surfactant is also preferably a surfactant formed by linking an alcohol with a fatty acid via ester bonding or amide bonding. In this case, the molecular weight of the alcohol is preferably 70 g/mol or more, more preferably 80 g/mol or more, preferably 330 g/mol or less, more preferably 300 g/mol or less, still more preferably 250 g/mol or less, particularly preferably 200 g/mol or less.

When the molecular weight of the alcohol is equal to or more than the lower limit described above, the coatability of the core portion with the shell portion will be further enhanced. Accordingly, it is possible to obtain a core-shell structure having a further enhanced immediate effect in transdermal absorption. When the molecular weight of the alcohol is equal to or less than the upper limit described above, the releasability of the active ingredient from particles in the body further increases. Accordingly, it is possible to obtain a core-shell structure having a further enhanced immediate effect in transdermal absorption. When an alcohol is linked with a fatty acid via amide bonding, an alkanolamine is regarded to be linked with the fatty acid via amide bonding. Accordingly, in this case, the molecular weight of the alcohol means the molecular weight of the alkanolamine.

With reference to FIG. 2, the hydrophilic moiety and hydrophobic moiety of a surfactant formed by an alcohol and a fatty acid linked via ester bonding will be described hereinbelow. As shown in FIG. 2, when the alcohol is linked with the fatty acid via ester bonding, the portion surrounded by a dotted line in FIG. 2 is the hydrophobic moiety. The number of carbon atoms in the hydrocarbon group is the number of carbon atoms contained in R in the hydrophobic moiety. Accordingly, also when R in the hydrophobic moiety contains an ether bond or the like, the number of carbon atoms contained in R in the hydrophobic moiety is only determined. The portion surrounded by a long dashed short dashed line in FIG. 2 is the hydrophilic moiety. The alcohol moiety is R'O in the hydrophilic moiety. The original alcohol is thus represented by R'OH. Then, in this case, the molecular weight of the alcohol described above is the molecular weight of R'OH.

With reference to FIG. 3, the hydrophilic moiety and hydrophobic moiety of a surfactant formed by an alcohol and a fatty acid linked via amide bonding will be now described. As shown in FIG. 3, when the alcohol is linked with a fatty acid via amide bonding, the portion surrounded by a dotted line in FIG. 3 is the hydrophobic moiety. The number of carbon atoms in the hydrocarbon group is the number of carbon atoms contained in R in the hydrophobic moiety. Accordingly, also when R in the hydrophobic moiety contains an ether bond or the like, the number of carbon atoms contained in R in the hydrophobic moiety is only determined. The portion surrounded by a long dashed short dashed line in FIG. 3 is the hydrophilic moiety. The alcohol moiety is R'R"N in the hydrophilic moiety. The original alcohol is thus represented by R'R"NH. Then, in this case, the molecular weight of the alcohol described above is the molecular weight of R'R"NH.

The surfactant preferably contains at least one selected from the group consisting of sorbitan fatty acid esters, glycerin fatty acid esters, propylene glycol fatty acid esters and fatty acid alkanolamides. Of these, from the viewpoint of simultaneously achieving the transdermal absorbability and low skin irritation at a further higher level, the surfactant preferably contains at least one selected from the group consisting of sorbitan fatty acid esters, glycerin fatty acid esters, and propylene glycol fatty acid esters.

Examples of the sorbitan fatty acid esters in the present invention include, but are not particularly limited to, esters of sorbitan and a fatty acid.

Examples of fatty acids include caproic acid, caprylic acid, capric acid, lauric acid, myristic acid, palmitic acid, stearic acid, behenic acid, undecylenic acid, ricinoleic acid, oleic acid, linoleic acid, linolenic acid, ricinoleic acid, erucic acid, beef tallow, lard, coconut oil, palm oil, palm kernel oil, olive oil, rapeseed oil, rice bran oil, soy oil, and castor oil.

Specifically, examples of sorbitan fatty acid esters include, from the viewpoint of further enhancing the immediate effect and absorbability of the active ingredient, preferably sorbitan monostearate (NIKKOL SO-10MV manufactured by Nippon Surfactant Industries, Co., Ltd.), sorbitan trioleate (NIKKOL SO-30V manufactured by Nippon Surfactant Industries, Co., Ltd.), sorbitan sesquioleate (NIKKOL SO-15MV manufactured by Nippon Surfactant Industries, Co., Ltd.), sorbitan monooleate (NIKKOL SO-10V manufactured by Nippon Surfactant Industries, Co., Ltd.), sorbitan monolaurate (NIKKOL SL-10 manufactured by Nippon Surfactant Industries, Co., Ltd.), coconut oil fatty acid sorbitan (EMALEX SPC-10 manufactured by NIHON EMULSION Co., Ltd.), and sorbitan laurate (RIKEMAL L-250A manufactured by RIKEN VITAMIN Co., Ltd.).

Examples of glycerin fatty acid esters in the present invention include, but are not particularly limited to, esters of glycerin and a fatty acid.

Glycerin may be polyglycerin. The degree of polymerization of polyglycerin is not particularly limited, and is preferably 5 or less, more preferably 4 or less, still more preferably 3 or less. Of these, as glycerin, monoglycerin, diglycerin, or triglycerin is preferable. Specifically, as a glycerin fatty acid ester, a monoglycerin fatty acid ester, a diglycerin fatty acid ester, or a triglycerin fatty acid ester is preferable. In this case, it is possible to further enhance the immediate effect in transdermal absorption of the active ingredient.

Examples of fatty acids include caproic acid, caprylic acid, capric acid, lauric acid, myristic acid, palmitic acid, stearic acid, behenic acid, undecylenic acid, ricinoleic acid, oleic acid, linoleic acid, linolenic acid, ricinoleic acid, erucic acid, beef tallow, lard, coconut oil, palm oil, palm kernel oil, olive oil, rapeseed oil, rice bran oil, soy oil, and castor oil.

Specific examples of glycerin fatty acid esters include, from the viewpoint of further enhancing the immediate effect and transdermal absorbability of the active ingredient, preferably diglyceryl monostearate (NIKKOL DGMS manufactured by Nippon Surfactant Industries, Co., Ltd.), glyceryl monostearate (NIKKOL MGS-BMV manufactured by Nippon Surfactant Industries, Co., Ltd.), glyceryl monostearate (NIKKOL MGS-AMV manufactured by Nippon Surfactant Industries, Co., Ltd.), glyceryl monostearate (NIKKOL MGS-DEXV manufactured by Nippon Surfactant Industries, Co., Ltd.), glyceryl monostearate (NIKKOL MGS-ASEV manufactured by Nippon Surfactant Industries, Co., Ltd.), glyceryl monostearate (NIKKOL MGS-BSEV manufactured by Nippon Surfactant Industries, Co., Ltd.), glyceryl myristate (MGM manufactured by Nippon Surfactant Industries, Co., Ltd.), glyceryl tri(caprylate/caprate) (NIKKOL Triester F-810 manufactured by Nippon Surfactant Industries, Co., Ltd.), glyceryl monooleate (NIKKOL MGO manufactured by Nippon Surfactant Industries, Co., Ltd.), glyceryl monooleate (Capmul GMO-50 manufactured by ABITEC), glyceryl monoolivate (NIKKOL MGOL-70 manufactured by Nippon Surfactant Industries, Co., Ltd.), diglyceryl monooleate (NIKKOL DGMO-CV manufactured by Nippon Surfactant Industries, Co., Ltd.), diglyceryl monooleate (NIKKOL DGMO-90V manufactured by Nippon Surfactant Industries, Co., Ltd.), glyceryl monocaprylate (Sunsoft No. 700P-2-C manufactured by Taiyo Kagaku Co., Ltd.), glyceryl monocaprylate (Capmul 808G manufactured by ABITEC), glyceryl monocaprylate (Capmul MCM C8 manufactured by ABITEC), glyceryl monocaprate (Sunsoft No. 760-C manufactured by Taiyo Kagaku Co., Ltd.), glyceryl caprate (Capmul MCM C10 manufactured by ABITEC), glyceryl caprylate/caprate (Capmul MCM manufactured by ABITEC), glyceryl caprylate/caprate (Capmul 471 manufactured by ABITEC), mono/diglyceride caprate (Sunsoft No. 707-C manufactured by Taiyo Kagaku Co., Ltd.), diglyceride caprate (Sunfat GDC-S manufactured by Taiyo Kagaku Co., Ltd.), glyceryl monolaurate (Sunsoft No. 750-C manufactured by Taiyo Kagaku Co., Ltd.), and glyceryl monoundecylenate (NIKKOL MGU manufactured by Nippon Surfactant Industries, Co., Ltd.).

More preferable examples of glycerin fatty acid esters include glyceryl monooleate (NIKKOL MGO, glyceryl monooleate (Capmul GMO-50 manufactured by ABITEC) manufactured by Nippon Surfactant Industries, Co., Ltd.), glyceryl monoolivate (NIKKOL MGOL-70 manufactured by Nippon Surfactant Industries, Co., Ltd.), diglyceryl monooleate (NIKKOL DGMO-CV manufactured by Nippon Surfactant Industries, Co., Ltd.), diglyceryl monooleate (NIKKOL DGMO-90V manufactured by Nippon Surfactant Industries, Co., Ltd.), glyceryl monocaprylate (Sunsoft No. 700P-2-C manufactured by Taiyo Kagaku Co., Ltd.), glyceryl monocaprylate (Capmul 808G manufactured by ABITEC), glyceryl monocaprylate (Capmul MCM C8 manufactured by ABITEC) glyceryl monocaprate (Sunsoft No. 760-C manufactured by Taiyo Kagaku Co., Ltd.), glyceryl caprate (Capmul MCM C10 manufactured by ABITEC), glyceryl caprylate/caprate (Capmul MCM manufactured by ABITEC), glyceryl caprylate/caprate (Capmul 471 manufactured by ABITEC), mono/diglyceride caprate (Sunsoft No. 707-C manufactured by Taiyo Kagaku Co., Ltd.), diglyceride caprate (Sunfat GDC-S manufactured by Taiyo Kagaku Co., Ltd.), glyceryl monolaurate (Sunsoft No. 750-C manufactured by Taiyo Kagaku Co., Ltd.), and glyceryl monoundecylenate (NIKKOL MGU manufactured by Nippon Surfactant Industries, Co., Ltd.).

Examples of propylene glycol fatty acid esters in the present invention include, but are not particularly limited to, esters of propylene glycol and a fatty acid.

Examples of fatty acids include caproic acid, caprylic acid, capric acid, lauric acid, myristic acid, palmitic acid, stearic acid, behenic acid, undecylenic acid, ricinoleic acid, oleic acid, linoleic acid, linolenic acid, ricinoleic acid, erucic acid, beef tallow, lard, coconut oil, palm oil, palm kernel oil, olive oil, rapeseed oil, rice bran oil, soy oil, and castor oil.

Specific examples of propylene glycol fatty acid esters include, from the viewpoint of further enhancing the immediate effect and transdermal absorbability of the active ingredient, preferably propylene glycol monostearate (RIKEMAL PS-100 manufactured by RIKEN VITAMIN Co., Ltd.), propylene glycol monostearate (NIKKOL PMS-1CV manufactured by Nippon Surfactant Industries, Co., Ltd.), propylene glycol diisostearate (EMALEX PG-di-IS, manufactured by NIHON EMULSION Co., Ltd.), propylene glycol distearate (EMALEX PG-di-S manufactured by NIHON EMULSION Co., Ltd.), preferably propylene glycol monolaurate (RIKEMAL PL-100 manufactured by RIKEN VITAMIN Co., Ltd.), propylene glycol monooleate (RIKEMAL PO-100 manufactured by RIKEN VITAMIN Co., Ltd.), propylene glycol dioleate (EMALEX PG-di-O manufactured by NIHON EMULSION Co., Ltd.), propylene glycol dicaprylate (NIKKOL SEFSOL-228 manufactured by Nippon Surfactant Industries, Co., Ltd.), and propylene glycol dilaurate (EMALEX PG-M-L, manufactured by NIHON EMULSION Co., Ltd.).

Fatty acid alkanolamides in the present invention refer to ones that have a structure in which a R—CO group and two —CH$_2$CH$_2$OH groups are linked to N at the center and are represented by a chemical formula of R—CON(CH$_2$CH$_2$OH)$_2$.

Specific examples of fatty acid alkanolamides include oleic acid diethanolamide, lauric acid diethanolamide, lauric acid monoisopropanolamide, stearic acid diethanolamide, stearic acid monoethanolamide, stearic acid monoisopropanolamide, lauric acid myristic acid diethanolamide, palmitic acid monoethanolamide, coconut oil fatty acid diethanolamide, coconut oil fatty acid monoisopropanolamide, coconut oil fatty acid N-methyl ethanolamide, coconut oil fatty acid monoethanolamide, and palm kernel oil fatty acid diethanolamide. From the viewpoint of further enhancing skin permeability, fatty acid alkanolamides are preferably diethanolamides such as oleic acid diethanolamide, lauric acid diethanolamide, and coconut oil fatty acid diethanolamide.

The surfactant of the present invention may further contain surfactants other than sorbitan fatty acid esters, glycerin fatty acid esters, propylene glycol fatty acid esters, and fatty acid alkanolamides, and such surfactants can be appropriately selected depending on the application. Such surfactants can be selected from a wide variety of surfactants that can be used as medicaments and cosmetics. A plurality of surfactants may be used in combination.

Surfactants other than sorbitan fatty acid esters, glycerin fatty acid esters, propylene glycol fatty acid esters, and fatty acid alkanolamides may be any of nonionic surfactants, anionic surfactants, cationic surfactants, and amphoteric surfactants.

Examples of nonionic surfactants include, but are not particularly limited to, fatty acid esters, fatty alcohol ethoxylates, polyoxyethylene alkyl phenyl ethers, alkyl glycosides, polyoxyethylene castor oil, and hydrogenated castor oil.

Examples of the fatty acid esters include, but are not particularly limited to, esters of at least one of glycerin, polyglycerin, polyoxyethylene glycerin, polyoxyethylene, sorbitan, propylene glycol, and polyoxyethylene sorbit with a fatty acid such as caproic acid, caprylic acid, capric acid, lauric acid, myristic acid, palmitic acid, stearic acid, behenic acid, undecylenic acid, ricinoleic acid, oleic acid, linoleic acid, linolenic acid, ricinoleic acid, erucic acid, beef tallow, lard, coconut oil, palm oil, palm kernel oil, olive oil, rapeseed oil, rice bran oil, soy oil, and castor oil.

Examples of the anionic surfactants include alkyl sulfate salts, polyoxyethylene alkyl ether sulfate salts, alkyl benzene sulfonate salts, fatty acid salts, and phosphate salts.

Examples of the cationic surfactants include alkyl trimethyl ammonium salts, dialkyl dimethyl ammonium salts, alkyl dimethyl benzyl ammonium salts, and amine salts.

Examples of the amphoteric surfactants include alkyl amino fatty acid salts, alkyl betaines, and alkyl amine oxides.

As surfactants other than sorbitan fatty acid esters, glycerin fatty acid esters, propylene glycol fatty acid esters, and fatty acid alkanolamides, sucrose fatty acid esters, polyoxyethylene glycerin fatty acid esters, sorbitan fatty acid esters, polyoxyethylene sorbit fatty acid esters, polyoxyethylene castor oil, and hydrogenated castor oil are particularly preferable.

The surfactants other than sorbitan fatty acid esters, glycerin fatty acid esters, propylene glycol fatty acid esters, and fatty acid alkanolamides may be ones having a hydrocarbon chain such as an alkyl chain, alkenyl chain, or alkynyl chain.

The content of the surfactant can be set appropriately within a range where an effect of the present invention is exerted. The mass ratio to the active ingredient (active ingredient:surfactant) is preferably 1:0.5 to 1:100, more preferably 1:5 to 1:100. In this case, it is possible to further enhance the immediate effect of the active ingredient in the core-shell structure and formulations containing the core-shell structure. From the viewpoint of further enhancing the immediate effect of the active ingredient, the mass ratio between the active ingredient and the surfactant (active ingredient:surfactant) is preferably 1:0.5 to 1:50, more preferably 1:0.5 to 1:30. From the viewpoint of further enhancing the immediate effect of the active ingredient, the mass ratio between the active ingredient and the surfactant (active ingredient:surfactant) is preferably 1:5 to 1:50, more preferably 1:5 to 1:30.

In the present invention, the mass ratio between the active ingredient and the surfactant (active ingredient:surfactant) may also be 1:0.5 to 1:2. Usually, in a tape preparation, a higher content of the active ingredient tends to degrade the dispersibility of the active ingredient into the tape preparation. However, in the present invention, a surfactant having the HLB value described above and a saturated hydrocarbon group or an unsaturated hydrocarbon group is used, and thus it is possible to further enhance the dispersibility into the tape preparation even if the content of the active ingredient is high.

(Other Additive Components)

The core-shell structure may contain at least one other component in addition to the active ingredient and surfactant. Examples of the other components include, but are not particularly limited to, a stabilizing agent, a transdermal absorption enhancer, a skin irritation reducing agent, an antiseptic, and an analgesic.

The stabilizing agent has an action of stabilizing a particle structure. The stabilizing agent prevents unintentional early disintegration of the particle structure, and plays a role in further enhancing a sustained releasing effect of the active ingredient.

Examples of the stabilizing agents include, but are not particularly limited to, polysaccharides, proteins, and hydrophilic polymer materials. One or two or more stabilizing agents may be contained. The content of the stabilizing agent can be set appropriately depending on the type thereof. The stabilizing agent can be formulated so that, for example, the weight ratio between the active ingredient and the stabilizing agent (active ingredient:stabilizing agent) is from 1:0.1 to 1:10.

Examples of the transdermal absorption enhancers include, but are not particularly limited to, higher alcohols, N-acyl sarcosine and salts thereof, higher monocarboxylic acids, higher monocarboxylic acid esters, aromatic monoterpene fatty acid esters, dicarboxylic acids having 2 to 10 carbon atoms and salts thereof, polyoxyethylene alkyl ether phosphoric acid esters and salts thereof, lactic acid, lactic acid esters, and citric acid. One or two or more transdermal absorption enhancers may be contained. The content of the transdermal absorption enhancer can be set appropriately depending on the type thereof. The transdermal absorption enhancer can be formulated so that, for example, the weight ratio between the active ingredient and the transdermal absorption enhancer (active ingredient:transdermal absorption enhancer) is 1:0.01 to 1:50.

Examples of the skin irritation reducing agents include, but are not particularly limited to, hydroquinone glycosides, pantethine, tranexamic acid, lecithin, titanium oxide, aluminum hydroxide, sodium nitrite, sodium hydrogen nitrite, soybean lecithin, methionine, glycyrrhetinic acid, BHT, BHA, vitamin E and derivatives thereof, vitamin C and derivatives thereof, benzotriazole, propyl gallate, and mercaptobenzimidazole. One or two or more skin irritation reducing agents may be contained. The content ratio of the skin irritation reducing agent can be set appropriately depending on the types thereof. The skin irritation reducing agent can be formulated such that its content reaches 0.1% by weight to 50% by weight, for example, relative to the entire core-shell structure.

Examples of the antiseptics include, but are not particularly limited to, methyl paraoxybenzoate, propyl paraoxybenzoate, phenoxy ethanol, and thymol. The content ratio of the antiseptic in the core portion can be set appropriately depending on the type thereof. The antiseptic can be formulated such that its content reaches 0.01% by weight to 10% by weight, for example, relative to the entire core-shell structure. One or two or more antiseptics may be contained.

Examples of the analgesics include, but are not particularly limited to, local anesthetics, such as procaine, tetracaine, lidocaine, dibucaine, prilocaine, and salts thereof. One or two or more analgesics may be contained. The content ratio of the analgesic in the core-shell structure can be set appropriately depending on the types thereof. The analgesic can be formulated such that its content is 0.1% by weight to 30% by weight, for example, relative to the entire core-shell structure.

[Formulation]

A formulation of the present invention contains at least the core-shell structure described above. The formulation of the present invention, which contains at least the core-shell structure described above, has an excellent immediate effect in transdermal absorption of the active ingredient.

The content ratio of the core-shell structure described above in the formulation is not particularly limited. In the case of an adhesive preparation, ointment, cream, or gel, the content ratio of the core-shell structure is preferably 10% by weight or more and 70% by weight or less, more preferably 20% by weight or more and 50% by weight or less.

The mass ratio between the active ingredient and the surfactant (active ingredient:surfactant) in the formulation can be set appropriately within a range where an effect of the present invention is exerted, and is preferably 1:0.5 to 1:100, more preferably 1:5 to 1:100. In this case, it is possible to further enhance the immediate effect of the active ingredient in the core-shell structure and formulations containing the core-shell structure. From the viewpoint of further enhancing the immediate effect of the active ingredient, the mass ratio between the active ingredient and the surfactant (active ingredient:surfactant) is preferably 1:0.5 to 1:50, more preferably 1:0.5 to 1:30. From the viewpoint of further enhancing the immediate effect of the active ingredient, the mass ratio between the active ingredient and the surfactant (active ingredient:surfactant) is preferably 1:5 to 1:50, more preferably 1:5 to 1:30.

In the present invention, the mass ratio between the active ingredient and the surfactant (active ingredient:surfactant) is preferably 1:0.5 to 1:5, more preferably 1:0.5 to 1:2.5, still more preferably 1:0.5 to 1:2. Usually, in an adhesive preparation such as a tape preparation, a higher content of the active ingredient tends to degrade the dispersibility of the active ingredient into the adhesive preparation such as the tape preparation. However, in the present invention, a surfactant having the HLB value described above and a saturated hydrocarbon group or an unsaturated hydrocarbon group is used, and thus it is possible to further enhance the dispersibility into the adhesive preparation such as the tape preparation even if the content of the active ingredient is high. For this reason, it is possible to further enhance the skin permeability of the active ingredient.

The formulation of the present invention can be used in wide variety of applications intended for transdermal adsorption or transmucosal absorption, for example, external medicines such as external skin medicines, eye drops, nasal sprays, suppositories, and oral cavity drugs, cosmetics, and injections, depending on the type of the active ingredient.

The formulation of the present invention sustains its effect generally, but not particularly limited to, for 1 day to 1 week. In preferable embodiment, the formulation is used by once-a-day to once-a-week administration.

When the formulation of the present invention is an external medicine, a target disease differs depending on the type of the active ingredient.

The formulation of the present invention is not particularly limited and can be used as an adhesive preparation such as a tape preparation, for example, a plaster preparation or a tape preparation, for example, a plaster preparation (e.g., reservoir type or matrix type), a poultice, a patch, or a microneedle, an ointment, an external liquid preparation such as a liniment, or a lotion, a spray preparation such as an external aerosol or a pump spray preparation, a cream, a gel, an eye drop, an eye ointment, a nasal drop, a suppository, a semisolid formulation for rectal use, an enema formulation, oral agents, or an injection.

The formulation of the present invention preferably has a water content of 20% by mass or less, and more preferably contains substantially no water. This makes it possible to further enhance the shape retainability of the core-shell structure. In combination with the intrinsic shape retainability of the core-shell structure, elution of the active ingredient from the core-shell structure and even crystallization of the active ingredient can further be reduced. Consequently, the core-shell structure can exert further enhanced transdermal absorbability. From this viewpoint, the formulation of the present invention is preferably used as a preparation of which water content is adjusted to 20% by mass or less. The formulation of the present invention is more preferably used as a preparation containing substantially no water. The formulation of the present invention is preferably used as a plaster preparation, a patch, an ointment, or a gel.

(Base Phase)

The formulation of the present invention may contain a base phase, and the base phase may contain core-shell structures. In this case, such core-shell structures are preferably dispersed or dissolved in the base phase.

The base is not particularly limited and can be selected from a wide variety of bases that can be used as medicaments, in particular, external medicines, and cosmetics.

As described above, in the core-shell structure of the present invention, the core portion is solid. Thus, when the base phase is an oil phase, an S/O (Solid in Oil) type formulation can be formed by dispersing the core-shell structure in the oil phase of the base phase. The S/O type formulation can be obtained by, for example, dispersing particles obtained by a production method described below in the oil phase.

Once the S/O (Solid in Oil) type formulation is formed, the transparency of a coated sheet is enhanced when a base material is coated with the formulation. Once the S/O (Solid in Oil) type formulation is formed, in the case of X-ray diffraction measurement, for example, the diffraction pattern of the active ingredient is to be different from the diffraction of the original active ingredient singly. Compared with a coated sheet which is coated only with the active ingredient, the coated sheet of the S/O type formulation has a diffraction pattern in which at least one of a shift of the peak position, a change in the form, and a decrease in the peak intensity is observed. Particularly, with respect to the decrease in the peak intensity, the peak intensity of the active ingredient in the X-ray diffraction spectrum is to be deceased below the peak intensity of the active ingredient singly. In this case, the peak of the active ingredient may be lost because of the decrease.

The base is not particularly limited, and can be appropriately selected depending on the intended use from bases suitable for dispersing or dissolving the core-shell structure. A plurality of bases may be used in combination.

Examples of the bases include, but are not particularly limited to, oil bases and aqueous bases. Of these, the base is preferably an oil base. When the base is an oil base, a formulation having an S/O (Solid in Oil) type structure can be formed by dispersing the core-shell structures in the oil base. The formulation having an S/O (Solid in Oil) type structure can be produced by a method that includes a step of drying a W/O emulsion containing an active ingredient in the aqueous phase, for example, as described below.

Examples of the oil bases include vegetable oils, animal oils, neutral lipids, synthetic fats and oils, sterol derivatives, waxes, hydrocarbons, monoalcohol carboxylic acid esters, oxyacid esters, polyhydric alcohol fatty acid esters, silicones, higher alcohols, higher fatty acids, and fluorine-based oils. Examples of the aqueous bases include water and (polyhydric) alcohols.

Examples of the vegetable oils include, but are not particularly limited to, soy oil, sesame oil, olive oil, coconut oil, palm oil, rice oil, cotton seed oil, sunflower oil, rice bran oil, cacao butter, corn oil, safflower oil, castor oil, and rapeseed oil.

Examples of the animal oils include, but are not particularly limited to, mink oil, turtle oil, fish oil, beef oil, horse oil, pig oil, and shark squalane.

Examples of the neutral lipids include, but are not particularly limited to, triolein, trilinolein, trimyristin, tristearin, and triarachidonin.

Examples of the synthetic oils and fats include, but are not particularly limited to, phospholipid and azone.

Examples of the sterol derivatives include, but are not particularly limited to, dihydro cholesterol, lanosterol, dihydrolanosterol, phytosterol, cholic acid, and cholesteryl linoleate.

Examples of the waxes include candelilla wax, carnauba wax, rice wax, Japan wax, beeswax, montan wax, ozokerite, ceresin, paraffin wax, microcrystalline wax, petrolatum, Fischer-Tropsch wax, polyethylene wax, and ethylene-propylene copolymers.

Examples of the hydrocarbons include liquid paraffin (mineral oil), heavy liquid isoparaffin, light liquid isoparaffin, α-olefin oligomers, polyisobutene, hydrogenated polyisobutene, polybutene, squalane, olive-derived squalane, squalene, vaseline, and hard paraffin.

Examples of the monoalcohol carboxylic acid esters include octyldodecyl myristate, hexyldecyl myristate, octyldodecyl isostearate, cetyl palmitate, octyldodecyl palmitate, cetyl octanoate, hexyldecyl octanoate, isotridecyl isononanoate, isononyl isononanoate, octyl isononanoate, isotridecyl isononanoate, isodecyl neopentanoate, isotridecyl neopentanoate, isostearyl neopentanoate, octyldodecyl neodecanoate, oleyl oleate, octyldodecyl oleate, octyldodecyl ricinoleate, lanolin fatty acid octyldodecyl, hexyldecyl dimethyloctanoate, octyldodecyl erucate, hydrogenated castor oil isostearate, ethyl oleate, avocado oil fatty acid ethyl, isopropyl myristate, isopropyl palmitate, octyl palmitate, isopropyl isostearate, lanolin fatty acid isopropyl, diethyl sebacate, diisopropyl sebacate, dioctyl sebacate, diisopropyl adipate, dibutyl octyl sebacate, diisobutyl adipate, dioctyl succinate, and triethyl citrate.

Examples of the oxyacid esters include cetyl lactate, diisostearyl malate, and hydrogenated castor oil monoisostearate.

Examples of the polyalcohol fatty acid esters include glyceryl trioctanoate, glyceryl trioleate, glyceryl triisostearate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate/eicosadioate, trimethylolpropane trioctanoate, trimethylolpropane triisostearate, neopentylglycol dioctanoate, neopentylglycol dicaprate, 2-butyl-2-ethyl-1,3-propanediol dioctanoate, propylene glycol dioleate, pentaerythrityl tetraoctanoate, pentaerythrityl hydrogenated rosinate, ditrimethylolpropane triethyl hexanoate, ditrimethylolpropane (isostearate/sebacate), pentaerythrityl triethyl hexanoate, dipentaerythrityl (hydroxystearate/stearate/rosinate), diglyceryl diisostearate, polyglyceryl tetraisostearate, polyglyceryl-10 nonaisostearate, polyglyceryl-8 deca(erucate/isostearate/ricinoleate), (hexyldecanoic acid/sebacic acid) diglyceryl oligo ester, glycol distearate (ethylene glycol distearate), 3-methyl-1,5-pentanediol dineopentanoate, and 2,4-diethyl-1,5-pentanediol dineopentanoate.

Examples of the silicones include dimethicone (dimethylpolysiloxane), highly polymerized dimethicone (highly polymerized dimethylpolysiloxane), cyclomethicone (cyclodimethylsiloxane, decamethylcyclopentasiloxane), phenyl trimethicone, diphenyl dimethicone, phenyl dimethicone, stearoxypropyl dimethylamine, (aminoethylaminopropyl methicone/dimethicone)copolymers, dimethiconol, dimethiconol crosspolymers, silicone resins, silicone rubber, amino-modified silicones such as aminopropyl dimethicone and amodimethicone, cation-modified silicones, polyether-modified silicones such as dimethicone copolyol, polyglycerol-modified silicones, a sugar-modified silicones, carboxylic acid-modified silicones, phosphoric acid-modified silicones, sulfuric acid-modified silicones, alkyl-modified silicones, fatty acid-modified silicones, alkyl ether-modified silicones, amino acid-modified silicones, peptide-modified silicones, fluorine-modified silicones, cation-modified or polyether-modified silicones, amino-modified or polyether-modified silicones, alkyl-modified or polyether-modified silicones, and polysiloxane/oxyalkylene copolymers.

Examples of the higher alcohols include cetanol, myristyl alcohol, oleyl alcohol, lauryl alcohol, cetostearyl alcohol, stearyl alcohol, arachidyl alcohol, behenyl alcohol, jojoba alcohol, chimyl alcohol, selachyl alcohol, batyl alcohol, hexyldecanol, isostearyl alcohol, 2-octyldodecanol, and dimer diol.

Examples of the higher fatty acids include lauric acid, myristic acid, palmitic acid, stearic acid, isostearic acid, behenic acid, undecylenic acid, 12-hydroxystearic acid, palmitoleic acid, oleic acid, linoleic acid, linolenic acid, erucic acid, docosahexaenoic acid, eicosapentaenoic acid, isohexadecanoic acid, anteisoheneicosanoic acid, long-chain branched fatty acid, dimer acid, and hydrogenated dimer acid.

Examples of the fluorine-based oils include perfluorodecane, perfluorooctane, and perfluoropolyether.

Examples of the (polyhydric) alcohols include ethanol, isopropanol, glycerin, propylene glycol, 1,3-butylene glycol, and polyethylene glycol.

Furthermore, examples of the other bases include, but are not particularly limited to, bases used for adhesive preparations such as tape preparations, for example, plaster preparations or plaster preparations (e.g., reservoir type or matrix type), poultices, patches, and microneedles, ointments, external liquid preparations (e.g., liniments and lotions), spray preparations (e.g., external aerosols and pump spray preparations), creams, gels, eye drops, eye ointments, nasal drops, suppositories, semisolid formulations for rectal use, enema formulations, oral agents, and injections.

An example of the tape preparation of the present invention will be described hereinbelow with reference to FIG. 4.

FIG. 4 is a schematic cross-sectional view showing a tape preparation according to one embodiment of the present invention.

As shown in FIG. 4, the tape preparation 20 include a base material layer 21 and a pressure-sensitive adhesive layer 22. The pressure-sensitive adhesive layer 22 is layered on a surface 21a of the base material layer 21. A liner 23 is layered on the surface 22a of the pressure-sensitive adhesive layer 22.

The pressure-sensitive adhesive layer 22 may be layered on only the surface 21a on one side of the base material layer 21 or may be layered on both of the surfaces as this embodiment. The pressure-sensitive adhesive layer 22 of the tape preparation 20 contains the core-shell structure of the present invention described above. In a reservoir type or the like, the core-shell structure may not be contained not in the pressure-sensitive adhesive layer 22 but in a reservoir phase, for example.

The base material layer 21 is not particularly limited, so long as it supports the pressure-sensitive adhesive layer 22, and examples thereof include resin films, fibers, and non-woven fabrics. Examples of the resin films include films such as polyester and polyolefin films. The resin film is preferably a polyester film. Examples of polyesters include polyethylene terephthalate and polybutylene terephthalate, and polyethylene terephthalate is preferable.

A pressure-sensitive adhesive constituting the pressure-sensitive adhesive layer 22 is not particularly limited, and examples thereof include rubber pressure-sensitive adhesives, acrylic pressure-sensitive adhesives, and silicone pressure-sensitive adhesives. The pressure-sensitive adhesive constituting the pressure-sensitive adhesive layer 22 is preferably a rubber pressure-sensitive adhesive or acrylic pressure-sensitive adhesive, more preferably an acrylic pressure-sensitive adhesive.

The liner 23 is not particularly limited so long as it is one that protects the pressure-sensitive adhesive layer 22 until the tape preparation 20 is applied to the skin and is coated with silicone or the like, for example, so as to be easily released. Examples of the liner 23 include ones produced by coating polyethylene terephthalate or polypropylene with silicone. The liner 23 may not be provided. In formation of the pressure-sensitive adhesive layer 22, the pressure-sensitive adhesive may be applied to the base material 21 side or may be applied to the liner 23 side.

[Production Method]

The core-shell structure of the present invention can be produced by, but not particularly limited to, for example, a method that includes a step of drying a W/O emulsion containing an active ingredient in the aqueous phase.

The W/O emulsion is not particularly limited, so long as it is a so-called water in oil emulsion, and specifically it is an emulsion in which droplets of an aqueous solvent are dispersed in an oil solvent.

The W/O emulsion containing an active ingredient in an aqueous phase can be obtained by, for example, mixing an aqueous solvent, such as water and a buffer aqueous solution, containing an active ingredient, and an oil solvent, such as cyclohexane, hexane and toluene, containing a surfactant. The aqueous solvent containing an active ingredient may contain an additive component, such as a stabilizing agent, an absorption enhancer, or an irritation reducing agent, as needed, in addition to the active ingredient. The oil solvent containing a surfactant may contain an additive component, such as an irritation reducing agent, an analgesic, an absorption enhancer, or a stabilizing agent, as needed, in addition to a surfactant. A method for the mixing is not particularly limited, so long as it can form a W/O emulsion, and examples thereof include stirring with a homogenizer or the like.

The condition under stirring with a homogenizer is, for example, from about 5000 to about 50000 rpm, preferably from about 10000 to about 30000 rpm.

The mass ratio between the active ingredient and the surfactant (active ingredient:surfactant) in the W/O emulsion described above is preferably in the range of 1:0.5 to 1:100, more preferably in the range of 1:5 to 1:100. The mass ratio (active ingredient:surfactant) is still preferably in the range of 1:0.5 to 1:50, particularly preferably in the range of 1:5 to 1:50. The mass ratio (active ingredient:surfactant) is still preferably in the range of 1:0.5 to 1:30, particularly preferably in the range of 1:5 to 1:30. The mass ratio between the active ingredient and the surfactant (active ingredient:surfactant) may be 1:0.5 to 1:2.

A method for drying the W/O emulsion containing an active ingredient in an aqueous phase is not particularly limited, so long as it can remove the solvent (an aqueous solvent and an oil solvent) contained in the emulsion. Examples of methods for drying the W/O emulsion include freeze-drying, and vacuum-drying, preferably freeze-drying.

The method described above preferably further includes a step of heat-treating the W/O emulsion or a dried substance of the W/O emulsion from the viewpoint of a further reduction in the number average particle diameter of the core-shell structure to be obtained. A heat treatment temperature is, for example, 30° C. to 60° C., preferably 35° C. to 50° C., more preferably 35° C. to 45° C.

A heat treatment time is adjusted appropriately in accordance with the heat treatment temperature, and is, for example, 1 to 30 days, preferably 2 to 15 days, more preferably 3 to 7 days.

Examples of other methods for further reducing the number average particle diameter of the core-shell structure to be obtained include methods of subjecting the W/O emulsion or a dried substance of the W/O emulsion, after dispersion in a solvent or the like, as needed, to filtrate through a filter or the like or to centrifuge. In the case of filtration through a filter, a pore diameter of the filter is, for example, 1 µm or less, preferably 0.2 µm or less, more preferably 0.1 µm or less.

The core-shell structure of the present invention may be used as they are or may be used after being dispersed in the base described above or the like.

A formulation can be produced using the core-shell structure of the present invention, for example, by a solution coating method. In the solution coating method, additive components desired are further added, in addition to the core-shell structure of the present invention and a base, to a solvent so as to achieve a predetermined ratio. Then the mixture is stirred to prepare a homogeneous solution. Examples of the additive components described above include an absorption enhancer, a thickener, and a gelling agent. Examples of the solvents described above include hexane, toluene, and ethyl acetate. A concentration of the solid content in the solution is preferably 10% to 80% by mass, more preferably 20% to 60% by mass.

Then, the solution containing each of the components described above is evenly applied to a release liner, such as a silicone treated polyester film, using a coater such as a knife coater, a comma coater, or a reverse coater. After application, the solution was dried to form a drug-containing layer, a supporting material is laminated onto the layer, and then, a formulation can be obtained. Depending on the type of a support, after the drug-containing layer is formed on the support, and then a release liner can be laminated onto the surface of the drug-containing layer.

In another method, for example, additive components, such as a base, an absorption enhancer, a stabilizer, a thickener, and a gelling agent, are added to the core-shell structure of the present invention as needed, and mixed. After mixing, the mixture is retained by lamination or immersion on a natural woven member such as gauze or absorbent cotton, a synthetic fiber woven member such as polyester or polyethylene, or a woven fabric, a non-woven fabric or the like produced by appropriately combining the materials described above, or a permeable membrane or the like, depending on applications. Furthermore, the mixture retained can be covered with an adhesive cover material or the like and used.

The formulation thus obtained is cut into a shape of an ellipse, a circle, a square, a rectangle, or the like as needed, depending on the purpose of use. Alternatively, a pressure-sensitive adhesive layer or the like may be provided on the periphery of the formulation as needed.

Next, the present invention will become apparent by reference to specific examples and comparative examples of the present invention. Note that, the present invention is not limited to the following examples.

Example 1

Dissolved was 0.2 g of vardenafil hydrochloride hydrate (manufactured by Atomax Chemicals Co., Ltd., octanol/water partition coefficient: 0.0, molecular weight: 579 g/mol) in 40 g of pure water. To this solution, a solution obtained by dissolving 2.0 g of sorbitan monooleate (manufactured by Nippon Surfactant Industries, Co., Ltd., trade name "NIKKOL SO-10V", HLB value: 8.9, number of carbon atoms in the unsaturated hydrocarbon group: 17) in 80 g of cyclohexane was added, and the resultant solution was stirred with a homogenizer (25000 rpm, 2 minutes). Then, the solution was freeze dried for 2 days to obtain a core-shell structure.

Example 2

A core-shell structure was obtained in the same manner as in Example 1 except that sorbitan monooleate used in Example 1 was replaced by glyceryl monooleate (manufactured by Nippon Surfactant Industries, Co., Ltd., trade name "NIKKOL MGO", HLB value: 6.7, number of carbon atoms in the unsaturated hydrocarbon group: 17).

Example 3

A core-shell structure was obtained in the same manner as in Example 1 except that sorbitan monooleate used in Example 1 was replaced by sorbitan trioleate (manufactured by Nippon Surfactant Industries, Co., Ltd., trade name "NIKKOL SO-30V", HLB value: 5.1, number of carbon atoms in the unsaturated hydrocarbon group: 17).

Example 4

A core-shell structure was obtained in the same manner as in Example 1 except that sorbitan monooleate used in Example 1 was replaced by sorbitan monolaurate (manufactured by Nippon Surfactant Industries, Co., Ltd., trade name "NIKKOL SL-10", HLB value: 11.0, number of carbon atoms in the saturated hydrocarbon group: 11).

Example 5

A core-shell structure was obtained in the same manner as in Example 1 except that sorbitan monooleate used in Example 1 was replaced by glyceryl monocaprylate (manufactured by Taiyo Kagaku Co., Ltd., trade name "Sunsoft No. 700P-2-C", HLB value: 10.9, number of carbon atoms in the saturated hydrocarbon group: 7).

Example 6

A core-shell structure was obtained in the same manner as in Example 1 except that sorbitan monooleate used in Example 1 was replaced by glyceryl monocaprate (manufactured by Taiyo Kagaku Co., Ltd., trade name "Sunsoft No. 760-C", HLB value: 9.7, number of carbon atoms in the saturated hydrocarbon group: 9).

Example 7

A core-shell structure was obtained in the same manner as in Example 1 except that sorbitan monooleate used in Example 1 was replaced by glyceryl monoundecylenate (manufactured by Nippon Surfactant Industries, Co., Ltd., trade name "NIKKOL MGU", HLB value: 9.1, number of carbon atoms in the unsaturated hydrocarbon group: 10).

Example 8

A core-shell structure was prepared in the same manner as in Example 1 except that sorbitan monooleate used in Example 1 was replaced by coconut oil fatty acid diethanolamide (manufactured by NOF CORPORATION, trade name "STAFOAM DFC", HLB value: 9.2, number of carbon atoms in the saturated hydrocarbon group: 11).

Example 9

A core-shell structure was prepared in the same manner as in Example 1 except that sorbitan monooleate used in Example 1 was replaced by lauric acid diethanolamide (manufactured by NOF CORPORATION, trade name "STAFOAM DL", HLB value: 9.2, number of carbon atoms in the saturated hydrocarbon group: 11).

Comparative Example 1

A core-shell structure was obtained in the same manner as in Example 1 except that sorbitan monooleate used in Example 1 was replaced by sucrose erucic acid ester (manufactured by Mitsubishi-Chemical Foods Corporation, trade name "ER-290", HLB value: 2.0, number of carbon atoms in the unsaturated hydrocarbon group: 21).

Comparative Example 2

A core-shell structure was obtained in the same manner as in Example 1 except that sorbitan monooleate used in Example 1 was replaced by sucrose lauric acid ester (manufactured by Mitsubishi-Chemical Foods Corporation, trade name "L-195", HLB value: 1.0, number of carbon atoms in the saturated hydrocarbon group: 11).

Comparative Example 3

A core-shell structure was obtained in the same manner as in Example 1 except that sorbitan monooleate used in Example 1 was replaced by sucrose oleic acid ester (manufactured by Mitsubishi-Chemical Foods Corporation, trade name "O-170", HLB value: 1.0, number of carbon atoms in the unsaturated hydrocarbon group: 17).

Comparative Example 4

A core-shell structure was obtained in the same manner as in Example 1 except that sorbitan monooleate used in Example 1 was replaced by propylene glycol monostearate (manufactured by Nippon Surfactant Industries, Co., Ltd., trade name "NIKKOL PMS-1CV", HLB value: 6.0, number of carbon atoms in the saturated hydrocarbon group: 17).

Comparative Example 5

A core-shell structure was obtained in the same manner as in Example 1 except that sorbitan monooleate used in Example 1 was replaced by glycerin monostearate (manufactured by Nippon Surfactant Industries, Co., Ltd., trade name "NIKKOL MGS-AMV", HLB value: 6.6, number of carbon atoms in the saturated hydrocarbon group: 17).

Comparative Example 6

A core-shell structure was obtained in the same manner as in Example 1 except that sorbitan monooleate used in Example 1 was replaced by sorbitan monostearate (manufactured by Nippon Surfactant Industries, Co., Ltd., trade name "NIKKOL SS-10MV", HLB value: 8.9, number of carbon atoms in the saturated hydrocarbon group: 17).
(Evaluation)

The core-shell structures obtained in Examples 1 to 9 and Comparative Examples 1 to 6 were evaluated for skin permeability in hairless rats by the following test.
Hairless Rat Skin Permeability Test;

A formulation was produced by adding, mixing, and dispersing each of core-shell structures of Examples and Comparative Examples into liquid paraffin (manufactured by Wako Pure Chemical Industries, Ltd., density (20° C.): 0.800 to 0.835 g/ml) such that its content reached 20% by weight relative to the total weight of the formulation.

A piece of skin of a hairless rat (Japan SLC, Inc., taken out from 8-week-old HWY/Slc) was set in a drug skin permeability test cell (see FIG. 5). To the upper part of the device, 1.0 g (approximately 7.07 cm$^2$) of the formulation produced by the method described above was applied. A buffer was prepared by allowing distilled water to contain $5 \times 10^{-4}$ M $NaH_2PO_4$, $2 \times 10^{-4}$ M $Na_2HPO_4$, $1.5 \times 10^{-4}$ M NaCl, and 10 ppm gentamicin sulfate (G1658, manufactured by Wako Pure Chemical Industries, Ltd.) and adjusting the pH of the solution to 7.2 with NaOH, and placed in a receptor layer at the lower part. The device was set in a thermostatic chamber kept at 32° C. since the start of the test. At a predetermined time after the test was started, 1 ml of the liquid in the thermostatic chamber was taken from the receptor layer at the lower part of the device, and immediately afterwards 1 ml of liquid having the same composition was added to the layer. Methanol was added to each of the receptor liquid samples collected to extract lipid eluted or the like, and the extract was centrifuged. After the centrifugation, the concentration of the active ingredient in the supernatant was quantitatively determined by high performance liquid chromatography (HPLC). On the basis of the amount of the active ingredient quantitatively determined, the lag time and cumulative amount permeated through the skin over 24 hours were calculated.

As shown in FIG. 6, in a graph having the cumulative amount permeated through the skin on the vertical axis and the time on the horizontal axis, the lag time is the time read from a point on the horizontal axis at which the extrapolated straight-line section of the steady state crosses the horizontal axis.

The results are shown in Table 2 below. Table 2 shows the molecular weight of the hydrophilic moiety (molecular weight of hydrophilic moiety), molecular weight of the alcohol, HLB value, number of carbon atoms in the hydrocarbon group, and number of double bonds in the hydrocarbon group in each of the surfactants used in Examples 1 to 9 and Comparative Examples 1 to 6, respectively.

TABLE 2

| | Active ingredient | | Surfactant | | | | Hydrophilic moiety | Alcohol |
|---|---|---|---|---|---|---|---|---|
| | Name | Molecular weight (g/mol) | Name | Trade name | Number of hydrophobic chains bound | Fatty acid molecular weight | molecular weight (g/mol) | molecular weight (g/mol) |
| Example 1 | Vardenafil hydrochloride hydrate | 579 | Sorbitan monooleate | NIKKOL SO-10V | 1 | 282.5 | 191.2 | 164.2 |
| Example 2 | Vardenafil hydrochloride hydrate | 579 | Glyceryl monooleate | NIKKOL MGO | 1 | 282.5 | 119.1 | 92.1 |
| Example 3 | Vardenafil hydrochloride hydrate | 579 | Sorbitan trioleate | NIKKOL SO-30V | 3 | 282.5 | 245.2 | 164.2 |
| Example 4 | Vardenafil hydrochloride hydrate | 579 | Sorbitan monolaurate | NIKKOL SL-10 | 1 | 200.3 | 191.2 | 164.2 |
| Example 5 | Vardenafil hydrochloride hydrate | 579 | Glyceryl monocaprylate | Sunsoft No. 700P-2-C | 1 | 144.2 | 119.1 | 92.1 |
| Example 6 | Vardenafil hydrochloride hydrate | 579 | Glyceryl monocaprate | Sunsoft No. 760-C | 1 | 172.3 | 119.1 | 92.1 |
| Example 7 | Vardenafil hydrochloride hydrate | 579 | Glyceryl monoundecylenate | NIKKOL MGU | 1 | 186.3 | 119.1 | 92.1 |
| Example 8 | Vardenafil hydrochloride hydrate | 579 | Coconut oil fatty acid diethanolamide | STAFOAM DFC | 1 | 200.3 | 132.1 | 105.1 |
| Example 9 | Vardenafil hydrochloride hydrate | 579 | Lauric acid diethanolamide | STAFOAM DL | 1 | 200.3 | 132.1 | 105.1 |

TABLE 2-continued

| | | | | | | | | |
|---|---|---|---|---|---|---|---|---|
| Comparative Example 1 | Vardenafil hydrochloride hydrate | 579 | Sucrose erucic acid ester | ER-290 | 1-8 | 338.6 | 369-558 | 342.3 |
| Comparative Example 2 | Vardenafil hydrochloride hydrate | 579 | Sucrose lauric acid ester | L-195 | 1-8 | 200.3 | 369-558 | 342.3 |
| Comparative Example 3 | Vardenafil hydrochloride hydrate | 579 | Sucrose oleic acid ester | O-170 | 1-8 | 282.5 | 369-558 | 342.3 |
| Comparative Example 4 | Vardenafil hydrochloride hydrate | 579 | Propylene glycol monostearate | NIKKOL PMS-1CV | 1 | 284.5 | 103.1 | 76.1 |
| Comparative Example 5 | Vardenafil hydrochloride hydrate | 579 | Glycerin monostearate | NIKKOL MGS-AMV | 1 | 284.5 | 119.1 | 92.1 |
| Comparative Example 6 | Vardenafil hydrochloride hydrate | 579 | Sorbitan monostearate | NIKKOL SS-10MV | 1 | 284.5 | 191.2 | 164.2 |

| | Surfactant | | | | | | | Cumulative |
|---|---|---|---|---|---|---|---|---|
| | Total molecular weight (g/mol) | HLB value (Griffin method) | Number of carbon atoms in hydrocarbon group | Number of double bonds in hydrocarbon group | Core shell ratio | Formulation form | Lag time (hours) | amount permeated through the skin over 24 hours ($\mu g/cm^3$) |
| Example 1 | 428.6 | 8.9 | 17 | 1 | 1:10 | Solution | 10 | 58 |
| Example 2 | 356.5 | 6.7 | 17 | 1 | 1:10 | Solution | 10 | 129 |
| Example 3 | 957.5 | 5.1 | 17 | 1 | 1:10 | Solution | 6 | 30 |
| Example 4 | 346.5 | 11.0 | 11 | 0 | 1:10 | Solution | <3 | 594 |
| Example 5 | 218.3 | 10.9 | 7 | 0 | 1:10 | Solution | <3 | 658 |
| Example 6 | 246.3 | 9.7 | 9 | 0 | 1:10 | Solution | <3 | 847 |
| Example 7 | 260.4 | 9.1 | 10 | 1 | 1:10 | Solution | <3 | 1027 |
| Example 8 | 287.4 | 9.2 | 11 | 0 | 1:10 | Solution | <3 | 249 |
| Example 9 | 287.4 | 9.2 | 11 | 0 | 1:10 | Solution. | <3 | 247 |
| Comparative Example 1 | 663-2907 | 2.0 | 21 | 1 | 1:10 | Solution | 42 | 0 |
| Comparative Example 2 | 525-1801 | 1.0 | 11 | 0 | 1:10 | Solution | 18 | 3 |
| Comparative Example 3 | 607-2458 | 1.0 | 17 | 1 | 1:10 | Solution | 17 | 16 |
| Comparative Example 4 | 342.6 | 6.0 | 17 | 0 | 1:10 | Solution | ND | 0 |
| Comparative Example 5 | 358.6 | 6.6 | 17 | 0 | 1:10 | Solution | ND | 0 |
| Comparative Example 6 | 430.7 | 8.9 | 17 | 0 | 1:10 | Solution | ND | 0 |

As shown in Table 2, the core-shell structures of Comparative Examples 1 to 3 had a drug lag time (transdermal absorption delay time) of 17 hour or more. From the core-shell structures of Comparative Examples 4 to 6, no drug was transdermally absorbed. In contrast, the core-shell structures of Examples, which had a lag time of 10 hours or less, were particles that had an excellent immediate effect and high skin permeability.

Example 10

Dissolved was 0.2 g of loxoprofen sodium dihydrate (manufactured by Tokyo Chemical Industry Co., Ltd., octanol/water partition coefficient: 0.8, molecular weight: 304 g/mol) in 40 g of pure water. To this solution, a solution obtained by dissolving 1.0 g of sorbitan monooleate (manufactured by Nippon Surfactant Industries, Co., Ltd., trade name "NIKKOL SO-10V", HLB value: 8.9, number of carbon atoms in the unsaturated hydrocarbon group: 17) in 80 g of cyclohexane was added, and the resultant solution was stirred with a homogenizer (25000 rpm, 2 minutes). Then, the solution was freeze dried for 2 days to obtain a core-shell structure.

Example 11

A core-shell structure was obtained in the same manner as in Example 10 except that sorbitan monooleate used in Example 10 was replaced by glyceryl monooleate (manufactured by Nippon Surfactant Industries, Co., Ltd., trade name "NIKKOL MGO", HLB value: 6.7, number of carbon atoms in the unsaturated hydrocarbon group: 17).

Example 12

A core-shell structure was obtained in the same manner as in Example 10 except that sorbitan monooleate used in Example 10 was replaced by sorbitan trioleate (manufactured by Nippon Surfactant Industries, Co., Ltd., trade name "NIKKOL SO-30V", HLB value: 5.1, number of carbon atoms in the unsaturated hydrocarbon group: 17).

Example 13

A core-shell structure was obtained in the same manner as in Example 10 except that sorbitan monooleate used in Example 10 was replaced by sorbitan monolaurate (manufactured by Nippon Surfactant Industries, Co., Ltd., trade name "NIKKOL SL-10", HLB value: 11.0, number of carbon atoms in the saturated hydrocarbon group: 11).

Example 14

A core-shell structure was obtained in the same manner as in Example 10 except that sorbitan monooleate used in Example 10 was replaced by glyceryl monocaprylate (manufactured by Taiyo Kagaku Co., Ltd., trade name "Sunsoft No. 700P-2-C", HLB value: 10.9, number of carbon atoms in the saturated hydrocarbon group: 7).

Example 15

A core-shell structure was obtained in the same manner as in Example 10 except that sorbitan monooleate used in Example 10 was replaced by glyceryl monocaprate (manufactured by Taiyo Kagaku Co., Ltd., trade name "Sunsoft No. 760-C", HLB value: 9.7, number of carbon atoms in the saturated hydrocarbon group: 9).

Example 16

A core-shell structure was obtained in the same manner as in Example 10 except that sorbitan monooleate used in Example 10 was replaced by glyceryl monoundecylenate (manufactured by Nippon Surfactant Industries, Co., Ltd., trade name "NIKKOLMGU", HLB value: 9.2, number of carbon atoms in the unsaturated hydrocarbon group: 10).

Example 17

A core-shell structure was prepared in the same manner as in Example 10 except that sorbitan monooleate used in Example 10 was replaced by coconut oil fatty acid diethanolamide (manufactured by NOF CORPORATION, trade name "STAFOAM DFC", HLB value: 9.2, number of carbon atoms in the saturated hydrocarbon group: 11).

Example 18

A core-shell structure was prepared in the same manner as in Example 10 except that sorbitan monooleate used in Example 10 was replaced by lauric acid diethanolamide (manufactured by NOF CORPORATION, trade name "STAFOAM DL", HLB value: 9.2, number of carbon atoms in the saturated hydrocarbon group: 11).

(Evaluation)

The core-shell structures obtained in Examples 10 to 18 were evaluated for skin permeability in hairless rats and primary irritation on rabbit skin by the following tests. The results are shown in Table 3 below.

Hairless Rat Skin Permeability Test;

A formulation was produced by adding, mixing, and dispersing each of the core-shell structures of Examples 10 to 18 into an ointment base Plastibase (manufactured by Taisho Pharmaceutical Co., Ltd.) such that its content reached 20% by weight relative to the total weight of a formulation.

A piece of skin of a hairless rat (manufactured by Japan SLC, Inc., taken out from 8-week-old HWY/Slc) was set in a drug skin permeability test cell (see FIG. 5). To the upper part of the device, 1.0 g (7.07 cm$^2$) of the formulation produced by the method described above was applied. In a receptor layer at the lower part, a buffer was placed which was prepared by allowing distilled water to contain $5\times10^{-4}$ M $NaH_2PO_4$, $2\times10^{-4}$ M $Na_2HPO_4$, $1.5\times10^{-4}$ M NaCl, and 10 ppm gentamicin sulfate (G1658, manufactured by Wako Pure Chemical Industries, Ltd.) and adjusting the pH of the solution to 7.2 with NaOH. The device was set in a thermostatic chamber kept at 32° C. since the start of the test. At a predetermined time after the test was started, 1 ml of the liquid in the thermostatic chamber was taken from the receptor layer at the lower part of the device, and immediately afterwards 1 ml of liquid having the same composition was added to the layer. Methanol was added to each of the receptor liquid samples collected to extract lipid eluted or the like, and the extract was centrifuged. After the centrifugation, the concentration of the active ingredient in the supernatant was quantitatively determined by high performance liquid chromatography (HPLC). On the basis of the amount of the active ingredient quantitatively determined, the lag time and cumulative amount permeated through the skin over 24 hours were calculated in the same manner as described above.

Rabbit Skin Primary Irritation Test;

The dorsal skin of a rabbit was shaved with an electric clipper (with an electric shaver as required). Healthy skin at two points on either side of the dorsal mid-line of the dorsal skin, that is, four points in total, was used as administration sites. The formulation produced in the same manner as in the hairless rat skin permeability test was taken with a spatula and spread homogeneously on pieces of lint having a size of 2 cm×2 cm, and the lint pieces are attached to the administration sites. The lint pieces are fixed by covering the sites with a non-woven adhesive bandage (manufactured by Nichiban Co., Ltd., MESHPORE, No. 50). Then, the administration sites were altogether wrapped with gauze and then sealed by covering the sites with an adhesive cloth elastic bandage (manufactured by Nichiban Co., Ltd., ELASTPORE, No. 100). The sealing was terminated 24 hours after the start of the administration, and the administration specimens were removed.

Skin reaction at 24 hours after the administration (30 minutes after the sealing is terminated and the administration specimens are removed) was observed by the naked eye. Thereafter, skin reaction at 48 hours and 72 hours after the administration (30 minutes after the sealing was terminated and the administration specimens were removed) was observed by the naked eye in the same manner. The skin reaction evaluation was carried out based on the Draize scoring shown in Table 4 below.

Specifically, individual skin reaction scores (sum of erythema and eschar formation and edema formation) at the administration sites of each rabbit were calculated for each administration specimen at each observation time. Thereafter, the primary irritation index (primary irritation index; P.I.I.) was calculated from the individual scores at 24 hours and 72 hours after the administration (the score at 48 hours after the administration is not added). Specifically, the following equations (1) and (2) were used for the calculation.

$$\text{Average score of each administration site} = (\text{Sum of individual scores at 24 hours and 72 hours after the administration})/2 \quad \text{Equation (1)}$$

$$\text{Primary irritation index (P.I.I.)} = (\text{Sum of the average score of each administration site})/(3 (\text{rabbits})) \quad \text{Equation (2)}$$

From the primary irritation index (P.I.I.) obtained, the degree of irritation of each of the administration specimens was classified in accordance with the classification table of Table 5 below.

TABLE 3

|  | Surfactant name | Trade name | Lag time (hours) | Cumulative amount permeated through the skin over 24 hours (μg/cm$^2$) | Skin irritation (P.I.I.) |
| --- | --- | --- | --- | --- | --- |
| Example 10 | Sorbitan monooleate | NIKKOL SO-10V | <2.0 | 230 | 1.9 Slight irritation |
| Example 11 | Glyceryl monooleate | NIKKOL MGO | <2.0 | 473 | 1.8 Slight irritation |
| Example 12 | Sorbitan trioleate | NIKKOL SO-30V | 2.2 | 300 | 1.0 Slight irritation |
| Example 13 | Sorbitan monolaurate | NIKKOL SL-10 | 3.2 | 505 | 1.0 Slight irritation |
| Example 14 | Glyceryl monocaprylate | Sunsoft No. 700P-2-C | <2.0 | 881 | 0.5 Slight irritation |
| Example 15 | Glyceryl monocaprate | Sunsoft No. 760-C | <2.0 | 1079 | 2.0 Slight irritation |
| Example 16 | Glyceryl monoundecylenate | NIKKOL MGU | 2.6 | 548 | 1.0 Slight irritation |
| Example 17 | Coconut oil fatty acid diethanolamide | STAFOAM DFC | 2.6 | 1123 | 4.5 Moderate irritation |
| Example 18 | Lauric acid diethanolamide | STAFOAM DL | <2.0 | 548 | 4.5 Moderate irritation |

TABLE 4

| Degree of skin reaction | Score |
| --- | --- |
| Erythema and eschar formation | |
| No erythema | 0 |
| Very slight erythema (barely perceptible) | 1 |
| Slight erythema | 2 |
| Moderate to severe erythema | 3 |
| Crimson severe erythema and slight eschar formation (injuries in depth) | 4 |
| Edema formation | |
| No edema | 0 |
| Very slight edema (barely perceptible) | 1 |
| Slight edema (well defined) | 2 |
| Moderate edema (raised approximately 1 mm) | 3 |
| Severe edema (raised more than 1 mm and extending to the periphery) | 4 |

TABLE 5

| Primary irritation index (P.I.I.) | Safety classification |
| --- | --- |
| 0 | No irritation |
| 0 < P.I.I. ≤ 2 | Slight irritation |
| 2 < P.I.I. ≤ 5 | Moderate irritation |
| 5 < P.I.I. | Severe irritation |

As clearly seen from Table 3, it is possible to confirm that Examples 10 to 16 have an excellent immediate effect as well as can further reduce skin irritation, in transdermal absorption.

Example 19

Dissolved was 0.2 g of rivastigmine L-tartrate (manufactured by Tokyo Chemical Industry Co., Ltd., octanol/water partition coefficient: 2.3, molecular weight: 400 g/mol) in 10 g of pure water. To this solution, a solution obtained by dissolving 0.4 g of glyceryl monooleate (manufactured by Nippon Surfactant Industries, Co., Ltd., trade name "NIKKOL MGO", HLB value: 6.7, number of carbon atoms in the unsaturated hydrocarbon group: 17) in 20 g of cyclohexane was added, and the resultant solution was stirred with a homogenizer (25000 rpm, 2 minutes). Then, the solution was freeze dried for 2 days to obtain a core-shell structure.

To 60 parts by weight of the core-shell structure obtained, 40 parts by weight of an acrylic pressure-sensitive adhesive (manufactured by CosMED Pharmaceutical Co., Ltd., trade name "MAS683") was blended, and toluene was added to the mixture in such a manner that the concentration of solids reached 30% by weight. Then, the resultant was mixed to homogeneity to prepare a pressure-sensitive adhesive layer solution.

Then, a release sheet was provided which had been subjected to a mold release treatment by application of silicone onto a surface of a release base material made of a polyethylene terephthalate film having a thickness of 38 μm. The pressure-sensitive adhesive layer solution was applied onto the surface subjected to the mold release treatment of this release sheet and dried at 90° C. for 20 minutes to produce a laminate having a pressure-sensitive adhesive layer having a thickness of 110 μm formed on the surface of the release sheet subjected to the mold release treatment. Then, a support was provided made of a polyethylene terephthalate film having a thickness of 38 μm. One surface of this support and the pressure-sensitive adhesive layer of the laminate described above were superposed so as to be face to each other, and the support and the laminate was layered and integrated by transferring the pressure-sensitive adhesive layer of the laminate onto the support to thereby produce a tape preparation.

Example 20

A tape preparation was obtained in the same manner as in Example 19 except that glyceryl monooleate used in Example 19 was replaced by sorbitan monolaurate (manufactured by Nippon Surfactant Industries, Co., Ltd., trade name "NIKKOL SL-10", HLB value: 11.0, number of carbon atoms in the saturated hydrocarbon group: 11).

Example 21

A tape preparation was obtained in the same manner as in Example 19 except that glyceryl monooleate used in Example 19 was replaced by 0.2 g of glyceryl monocaprylate (manufactured by Taiyo Kagaku Co., Ltd., trade name "Sunsoft No. 700P-2-C", HLB value: 10.9, number of carbon atoms in the saturated hydrocarbon group: 7).

Comparative Example 7

A tape preparation was obtained in the same manner as in Example 19 except that glyceryl monooleate used in Example 19 was replaced by sucrose erucic acid ester (manufactured by Mitsubishi-Chemical Foods Corporation, trade name "ER-290", HLB value: 2.0, number of carbon atoms in the unsaturated hydrocarbon group: 21).

Comparative Example 8

A tape preparation was obtained in the same manner as in Example 19 except that 40 parts by weight of an acrylic pressure-sensitive adhesive (manufactured by CosMED Pharmaceutical Co., Ltd., trade name "MAS683") was blended as it was to 40 parts by weight of rivastigmine L-tartrate and 20 parts by weight of glyceryl monocaprylate, toluene was added to the mixture in such a manner that the concentration of solids reached 40% by weight, and then the resultant was mixed to homogeneity to thereby prepare a pressure-sensitive adhesive layer solution.

Comparative Example 9

A tape preparation was obtained in the same manner as in Example 19 except that 40 parts by weight of rivastigmine L-tartrate was blended as it was with 60 parts by weight of an acrylic pressure-sensitive adhesive (manufactured by CosMED Pharmaceutical Co., Ltd., trade name "MAS683"). (Evaluation)

The tape preparations obtained in Examples 19 to 21 and Comparative Example 7 were evaluated for skin permeability in hairless rats by the following test. Additionally, the tape preparations obtained in Example 21 and Comparative Examples 8 and 9 were evaluated for X-ray diffraction measurement by the following test.

Hairless Rat Skin Permeability Test; A piece of skin of a hairless rat (Japan SLC, Inc., taken out from 8-week-old HWY/Slc) was set in a drug skin permeability test cell (FIG. 5). To the upper part of the device, 1.33 cm² of each of the tape preparations produced in Examples and Comparative Note that, in Examples 19 to 21, although the content of the active ingredient was increased, it was confirmed that the coating property and dispersibility in the form of a tape preparation were enhanced.

X-Ray Diffraction Measurement;

The tape preparations of Example 21, Comparative Example 8, and Comparative Example 9 were measured by the X-ray diffraction method.

A crystalline state of the active ingredient was measured using an X-ray Diffractometer (manufactured by Rigaku Corporation, "SmartLab)). A concentration method optical arrangement was used, and a CuKα ray (wavelength: 1.54 Å) was used with power of 45 kV and 200 mA as the light source. A Soller slit 5.0° was used as the incident slit, and a Soller slit 5.0° was used as the receiving slit. The measurement was carried out every 0.02° in the scanning range of 5 to 40°. The count time was set to 5°/minute. The results are shown in FIG. 7.

As shown in FIG. 7, when the X-ray diffraction pattern of Comparative Example 8 was checked, the positions of the diffraction peaks corresponded to those of the diffraction peak observed in Comparative Example 9. When the X-ray diffraction pattern of Example 21 was checked, the diffraction peaks observed in Comparative Example 8 disappeared. It was confirmed that the active ingredient formed a core-shell structure also in the pressure-sensitive adhesive layer of the tape preparation.

TABLE 6

| | Name | Trade name | Hydrophilic moiety molecular weight (g/mol) | HLB value (Griffin method) | Number of carbon atoms in hydrocarbon group | Number of double bonds in hydrocarbon group | Core/shell ratio | Lag time (hours) | Cumulative amount permeated through the skin over 24 hours (μg/cm²) |
|---|---|---|---|---|---|---|---|---|---|
| Example 19 | Glyceryl monooleate | NIKKOL MGO | 119.1 | 6.7 | 17 | 1 | 1:2 | 4 | 60 |
| Example 20 | Sorbitan monolaurate | NIKKOL SL-10 | 191.2 | 11.0 | 11 | 0 | 1:2 | 8 | 27 |
| Example 21 | Glyceryl monocaprylate | Sunsoft No. 700P-2-C | 119.1 | 10.9 | 7 | 0 | 1:1 | 10 | 20 |
| Comparative Example 7 | Sucrose erucic acid ester | ER-290 | 369-558 | 2.0 | 21 | 1 | 1:2 | ND | 0 |

Examples was applied. A buffer was prepared by allowing distilled water to contain $5 \times 10^{-4}$ M $NaH_2PO_4$, $2 \times 10^{-4}$ M $Na_2HPO_4$, $1.5 \times 10^{-4}$ M NaCl, and 10 ppm gentamicin sulfate (G1658, manufactured by Wako Pure Chemical Industries, Ltd.) and adjusting the pH of the solution to 7.2 with NaOH, and placed in a receptor layer at the lower part. The device was set in a thermostatic chamber kept at 32° C. since the start of the test. At a predetermined time after the test was started, 1 ml of the liquid in the thermostatic chamber was taken from the receptor layer at the lower part of the device, and immediately afterwards 1 ml of liquid having the same composition was added to the layer. Methanol was added to each of the receptor liquid samples collected to extract lipid eluted or the like, and the extract was centrifuged. After the centrifugation, the concentration of the active ingredient in the supernatant was quantitatively determined by high performance liquid chromatography (HPLC). On the basis of the amount of the active ingredient quantitatively determined, the lag time and cumulative amount permeated through the skin over 24 hours were calculated in the same manner as described above. The results are shown in Table 6 below.

Example 22

A core-shell structure was obtained in the same manner as in Example 1 except that sorbitan monooleate used in Example 1 was replaced by diglyceride caprylate (manufactured by Taiyo Kagaku Co., Ltd., trade name "Sunfat GDC-S", HLB value: 13.2, number of carbon atoms in the saturated hydrocarbon group: 7).

Example 23

A core-shell structure was obtained in the same manner as in Example 1 except that sorbitan monooleate used in Example 1 was replaced by diglyceryl monooleate (manufactured by Nippon Surfactant Industries, Co., Ltd., trade name "NIKKOL DGMO-CV", HLB value: 9.0, number of carbon atoms in the unsaturated hydrocarbon group: 17).

Example 24

A core-shell structure was obtained in the same manner as in Example 1 except that sorbitan monooleate used in Example 1 was replaced by propylene glycol dioleate (manufactured by NIHON EMULSION Co., Ltd., trade name "EMALEX PG-di-O", HLB value: 4.3, number of carbon atoms in the unsaturated hydrocarbon group: 17).

Example 25

A core-shell structure was obtained in the same manner as in Example 1 except that sorbitan monooleate used in Example 1 was replaced by propylene glycol monolaurate (manufactured by RIKEN VITAMIN Co., Ltd., trade name "RIKEMAL PL-100", HLB value: 8.0, number of carbon atoms in the saturated hydrocarbon group: 11).

Example 26

Dissolved was 0.2 g of vardenafil hydrochloride hydrate (manufactured by Atomax Chemicals Co., Ltd., octanol/water partition coefficient: 0.0, molecular weight: 579 g/mol) in 40 g of pure water. To this solution, a solution obtained by dissolving 0.1 g of glyceryl monocaprylate (manufactured by Taiyo Kagaku Co., Ltd., trade name "Sunsoft No. 700P-2-C", HLB value: 10.9, number of carbon atoms in the saturated hydrocarbon group: 7) in 80 g of cyclohexane was added, and the resultant solution was stirred with a homogenizer (25000 rpm, 2 minutes). Then, the solution was freeze dried for 2 days to obtain a core-shell structure. Thereby the mass ratio (core shell ratio) between the active ingredient (vardenafil hydrochloride hydrate) and the surfactant (glyceryl monocaprylate) was set to 1:0.5.

Example 27

Dissolved was 0.2 g of vardenafil hydrochloride hydrate (manufactured by Atomax Chemicals Co., Ltd., octanol/water partition coefficient: 0.0, molecular weight: 579 g/mol) in 40 g of pure water. To this solution, a solution obtained by dissolving 4.0 g of glyceryl monocaprylate (manufactured by Taiyo Kagaku Co., Ltd., trade name "Sunsoft No. 700P-2-C", HLB value: 10.9, number of carbon atoms in the saturated hydrocarbon group: 7) in 80 g of cyclohexane was added, and the resultant solution was stirred with a homogenizer (25000 rpm, 2 minutes). Then, the solution was freeze dried for 2 days to obtain a core-shell structure. Thereby the mass ratio (core shell ratio) between the active ingredient (vardenafil hydrochloride hydrate) and the surfactant (glyceryl monocaprylate) was set to 1:20.

Example 28

A core-shell structure was obtained in the same manner as in Example 1 except that sorbitan monooleate used in Example 1 was replaced by glycerin palmitate (manufactured by Tokyo Chemical Industry Co., Ltd., trade name "Monopalmitin", HLB value: 7.2, number of carbon atoms in the saturated hydrocarbon group: 15).

Example 29

A core-shell structure was obtained in the same manner as in Example 1 except that sorbitan monooleate used in Example 1 was replaced by sorbitan palmitate (manufactured by Nippon Surfactant Industries, Co., Ltd., trade name "NIKKOLSP-10V", HLB value: 9.5, number of carbon atoms in the saturated hydrocarbon group: 15).

Example 30

A core-shell structure was obtained in the same manner as in Example 1 except that sorbitan monooleate used in Example 1 was replaced by glyceryl monolaurate (manufactured by Taiyo Kagaku Co., Ltd., trade name "Sunsoft No. 750-C". HLB value: 8.7, number of carbon atoms in the saturated hydrocarbon group: 11).

Example 31

Dissolved was 0.1 g of [Arg-8]-Vasopressin (manufactured by Heat-biochem Co., Ltd., octanol/water partition coefficient: −4.8, molecular weight: 1084 g/mol) in 40 g of pure water. To this solution, a solution obtained by dissolving 0.6 g of glyceryl monocaprate (manufactured by Taiyo Kagaku Co., Ltd., trade name "Sunsoft No. 760-C", HLB value: 9.7, number of carbon atoms in the saturated hydrocarbon group: 9) in 80 g of cyclohexane was added, and the resultant solution was stirred with a homogenizer (25000 rpm, 2 minutes). Then, the solution was freeze dried for 2 days to obtain a core-shell structure. Note that, the core shell ratio was set to 1:6.

Example 32

Dissolved was 0.1 g of Miravirsen (sequence name: antimir 122, manufactured by GeneDesign Inc., molecular weight: 4967 g/mol) in 40 g of pure water. To this solution, a solution obtained by dissolving 0.6 g of lauric acid diethanolamide (manufactured by NOF CORPORATION, trade name "STAFOAM DL", HLB value: 9.2, number of carbon atoms in the saturated hydrocarbon group: 11) in 80 g of cyclohexane was added, and the resultant solution was stirred with a homogenizer (25000 rpm, 2 minutes). Then, the solution was freeze dried for 2 days to obtain a core-shell structure. Note that, the core shell ratio was set to 1:6.

Example 33

Dissolved was 0.1 g of K3 Et-Free (B-class TLR9 ligand) (manufactured by GeneDesign Inc., molecular weight: 6349 g/mol) in 40 g of pure water. To this solution, a solution obtained by dissolving 0.6 g of lauric acid diethanolamide (manufactured by NOF CORPORATION, trade name "STAFOAM DL", HLB value: 9.2, number of carbon atoms in the saturated hydrocarbon group: 11) in 80 g of cyclohexane was added, and the resultant solution was stirred with a homogenizer (25000 rpm, 2 minutes). Then, the solution was freeze dried for 2 days to obtain a core-shell structure. Note that, the core shell ratio was set to 1:6.

Comparative Example 10

A core-shell structure was obtained in the same manner as in Example 1 except that sorbitan monooleate used in Example 1 was replaced by tetraglyceryl monooleate (manufactured by Nippon Surfactant Industries, Co., Ltd., trade name "NIKKOL Tetraglyn 1-OV", HLB value: 11.8, number of carbon atoms in the saturated hydrocarbon group: 17).

Comparative Example 11

A core-shell structure was obtained in the same manner as in Example 1 except that sorbitan monooleate used in Example 1 was replaced by hexaglycerin condensed ricinoleate (manufactured by Nippon Surfactant Industries, Co., Ltd., trade name "NIKKOL Hexaglyn PR-15", HLB value: 7.5, number of carbon atoms in the unsaturated hydrocarbon group: 53).

Comparative Example 12

A core-shell structure was obtained in the same manner as in Example 1 except that sorbitan monooleate used in Example 1 was replaced by tetraglycerin condensed ricinoleate (manufactured by Sakamoto Yakuhin Kogyo Co., Ltd., trade name "CR-310", HLB value: 7.8 or less, number of carbon atoms in the unsaturated hydrocarbon group: 35 or more).

Comparative Example 13

A core-shell structure was obtained in the same manner as in Example 1 except that sorbitan monooleate used in Example 1 was replaced by glycerin erucic acid ester (manufactured by Tokyo Chemical Industry Co., Ltd., trade name "Monoerucin", HLB value: 5.8, number of carbon atoms in the unsaturated hydrocarbon group: 21).

The core-shell structures obtained in Examples 22 to 31 and Comparative Examples 10 to 13 were subjected to skin permeability test in hairless rats in the same manner as in Example 1 to obtain the lag time and cumulative amount permeated through the skin over 24 hours. The results are shown in Table 7 below.

The core-shell structures obtained in Examples 32 to 33 were evaluated for skin permeability in hairless mice by the following test. The results are shown in Table 7 below.

Hairless Mouse Skin Permeability Test; A formulation was produced by adding, mixing, and dispersing each of core-shell structures of Examples 32 to 33 into liquid paraffin (manufactured by Wako Pure Chemical Industries, Ltd., density (20° C.): 0.800 to 0.835 g/ml) such that its content reached 20% by weight relative to the total weight of the formulation.

A piece of skin of a hairless mouse (manufactured by Japan SLC, Inc., taken out from 7-week-old Hos:HR-1) was set in a drug skin permeability test cell (see FIG. 5). To the upper part of the device, 1.0 g (7.07 cm$^2$) of the formulation produced by the method described above was applied. A buffer was prepared by allowing distilled water to contain $5\times10^{-4}$ M $NaH_2PO_4$, $2\times10^{-4}$ M $Na_2HPO_4$, $1.5\times10^{-4}$ M NaCl, and 10 ppm gentamicin sulfate (G1658, manufactured by Wako Pure Chemical Industries, Ltd.) and adjusting the pH of the solution to 7.2 with NaOH, and placed in a receptor layer at the lower part. The device was set in a thermostatic chamber kept at 32° C. since the start of the test. At a predetermined time after the test was started, 1 ml of the liquid in the thermostatic chamber was taken from the receptor layer at the lower part of the device, and immediately afterwards 1 ml of liquid having the same composition was added to the layer. Methanol was added to each of the receptor liquid samples collected to extract lipid eluted or the like, and the extract was centrifuged. After the centrifugation, the concentration of the active ingredient in the supernatant was quantitatively determined by high performance liquid chromatography (HPLC). On the basis of the amount of the active ingredient quantitatively determined, the lag time and cumulative amount permeated through the skin over 24 hours were calculated in the same manner as described above.

Example 34

The core-shell structure obtained in Example 5 was subjected to skin permeability test in hairless rats using an ointment base Plastibase in the same manner as in Example 10 to obtain the lag time and cumulative amount permeated through the skin over 24 hours. The results are shown in Table 7 below.

Comparative Example 14

The core-shell structure obtained in Comparative Example 1 was subjected to skin permeability test in hairless rats using an ointment base Plastibase in the same manner as in Example 10 to obtain the lag time and cumulative amount permeated through the skin over 24 hours. The results are shown in Table 7 below.

Example 35

The core-shell structure obtained in Example 5 was used to produce a tape preparation in the same manner as in Example 19, and the tape preparation was subjected to skin permeability test in hairless rats in the same manner as in Example 19 to obtain the lag time and cumulative amount permeated through the skin over 24 hours. The results are shown in Table 7 below.

TABLE 7

| | Active ingredient | | Surfactant | | | | |
|---|---|---|---|---|---|---|---|
| | Name | Molecular weight (g/mol) | Name | Trade name | Number of hydrophobic chains bound | Fatty acid molecular weight | Hydrophilic moiety molecular weight (g/mol) |
| Example 22 | Vardenafil hydrochloride hydrate | 579 | Diglyceride caprylate | Sunfat GDC-S | 1 | 144.2 | 193.0 |
| Example 23 | Vardenafil hydrochloride hydrate | 579 | Diglyceryl monooleate | NIKKOL DGMO-CV | 1 | 282.5 | 193.0 |
| Example 24 | Vardenafil hydrochloride hydrate | 579 | Propylene glycol dioleate | EMALEX PG-di-O | 2 | 282.55 | 130.1 |
| Example 25 | Vardenafil hydrochloride hydrate | 579 | Propylene glycol monolaurate | RIKEMAL PL-100 | 1 | 200.3 | 103.1 |
| Example 26 | Vardenafil hydrochloride hydrate | 579 | Glyceryl monocaprylate | Sunsoft No. 700P-2-C | 1 | 144.2 | 119.1 |

TABLE 7-continued

| | | | | | | | |
|---|---|---|---|---|---|---|---|
| Example 27 | Vardenafil hydrochloride hydrate | 579 | Glyceryl monocaprylate | SunSoft No. 700P-2-C | 1 | 144.2 | 119.1 |
| Example 28 | Vardenafil hydrochloride hydrate | 579 | Glycerin palmitate | Monopalmitin | 1 | 256.4 | 119.1 |
| Example 29 | Vardenafil hydrochloride hydrate | 579 | Sorbitan palmitate | NIKKOL SP-10V | 1 | 256.4 | 191.2 |
| Example 30 | Vardenafil hydrochloride hydrate | 579 | Glyceryl monolaurate | Sunsoft No. 750-C | 1 | 200.0 | 119.1 |
| Example 31 | [Arg-8]-Vasopression | 1084 | Glyceryl monocaprate | SunSoft No. 760-C | 1 | 172.3 | 119.1 |
| Example 32 | Miravirsen (sequence name: antimir 122) | 4967 | Lauric acid diethanolamide | STAFOAM DL | 1 | 200.3 | 132.1 |
| Example 33 | K3 Et-Free (B-class TLR9 ligand) | 6349 | Lauric acid diethanolamide | STAFOAM DL | 1 | 200.3 | 132.1 |
| Example 34 | Vardenafil hydrochloride hydrate | 579 | Glyceryl monocaprylate | Sunsoft No. 700P-2-C | 1 | 144.2 | 119.1 |
| Example 35 | Vardenafil hydrochloride hydrate | 579 | Glyceryl monocaprylate | Sunsoft No. 700P-2-C | 1 | 144.2 | 119.1 |
| Comparative Example 10 | Vardenafil hydrochloride hydrate | 579 | Tetraglyceryl monooleate | NIKKOL Tetraglyn 1-OV | 1 | 282.5 | 341.0 |
| Comparative Example 11 | Vardenafil hydrochloride hydrate | 579 | Hexaglycerin condensed ricinoleate | NIKKOL Hexaglyn PR-15 | 1 | 859.4 | 488.9 |
| Comparative Example 12 | Vardenafil hydrochloride hydrate | 579 | Tetraglycerin condensed ricinoleate | CR-310 | 1 | 578.9 | 341.0 |
| Comparative Example 13 | Vardenafil hydrochloride hydrate | 579 | Glycerin erucic acid ester | Monoerucin | 1 | 338.6 | 119.1 |
| Comparative Example 14 | Vardenafil hydrochloride hydrate | 579 | Sucrose erucic acid ester | ER-290 | 1-8 | 338.6 | 369-558 |

| | Surfactant | | | | | | | Cumulative amount |
|---|---|---|---|---|---|---|---|---|
| | Alcohol molecular weight (g/mol) | Total molecular weight (g/mol) | HLB value (Griffin method) | Number of carbon atoms in hydrocarbon group | Number of double bonds in hydrocarbon group | Core shell ratio | Formulation form | Lag time (hours) | permeated through the skin over 24 hours (μg/cm³) |
| Example 22 | 166.0 | 292.2 | 13.2 | 7 | 0 | 1:10 | Solution | <3 | 101 |
| Example 23 | 166.0 | 430.4 | 9.0 | 17 | 1 | 1:10 | Solution | 9 | 4 |
| Example 24 | 76.1 | 605.0 | 4.3 | 17 | 1 | 1:10 | Solution | 8 | 6 |
| Example 25 | 76.1 | 258.4 | 8.0 | 11 | 0 | 1:10 | Solution | 4 | 131 |
| Example 26 | 92.1 | 218.3 | 10.9 | 7 | 0 | 1:0.5 | Solution | <3 | 1893 |
| Example 27 | 92.1 | 218.3 | 10.9 | 7 | 0 | 1:20 | Solution | <3 | 400 |
| Example 28 | 92.3 | 330.5 | 7.2 | 15 | 0 | 1:10 | Solution | 12 | 4 |
| Example 29 | 164.2 | 402.6 | 9.5 | 15 | 0 | 1:10 | Solution | 8 | 4 |
| Example 30 | 92.1 | 274.1 | 8.7 | 11 | 0 | 1:10 | Solution | <3 | 1547 |
| Example 31 | 92.1 | 246.3 | 9.7 | 9 | 0 | 1:6 | Solution | <3 | 68 |
| Example 32 | 105.1 | 287.4 | 9.2 | 11 | 0 | 1:6 | Solution | 12 | 11 |
| Example 33 | 105.1 | 287.4 | 9.2 | 11 | 0 | 1:6 | Solution | 12 | 28 |
| Example 34 | 92.1 | 218.3 | 10.9 | 7 | 0 | 1:10 | Ointment | 6 | 271 |
| Example 35 | 92.1 | 218.3 | 10.9 | 7 | 0 | 1:10 | Tape preparation | 6 | 36 |
| Comparative Example 10 | 314.0 | 578.4 | 11.1 | 17 | 0 | 1:10 | Solution | 17 | 1 |
| Comparative Example 11 | 461.9 | 1301.3 | 7.5 | 53 | 3 | 1:10 | Solution | 17 | 2 |
| Comparative Example 12 | 314.0 | 874.8 | 7.8 or less | 35 or more | 2 or more | 1:10 | Solution | 20 | 1 |
| Comparative Example 13 | 92.1 | 412.7 | 5.8 | 21 | 1 | 1:10 | Solution | 18 | 4 |
| Comparative Example 14 | 342.3 | 663-2907 | 2.0 | 21 | 1 | 1:10 | Ointment | 18 | 1 |

REFERENCE SIGNS LIST

1 Parafilm
2 Skin
3 Formulation
4 Receptor liquid (pH=7.2 phosphate buffer)
5 Stirrer
10 Core-shell structure
11 Core portion
12 Shell portion
20 Tape preparation
21 Base material layer
21a, 22a Surface
22 Pressure-sensitive adhesive layer
23 Liner

The invention claimed is:

1. A tape preparation comprising a base material layer and a pressure-sensitive adhesive layer,
wherein
the pressure-sensitive adhesive layer comprising a core-shell structure and an acrylic pressure-sensitive adhesive,
the core-shell structure comprising:
a core portion containing an active ingredient, and
a shell portion containing a surfactant having an HLB value of 4 to 14,
the core portion being solid,
the surfactant containing a saturated hydrocarbon group having 7 to 15 carbon atoms or an unsaturated hydrocarbon group having 7 to 17 carbon atoms,
the surfactant comprising at least one selected from the group consisting of sorbitan fatty acid esters, glycerin fatty acid esters, and propylene glycol fatty acid esters, and
a mass ratio between the active ingredient and the surfactant (active ingredient:surfactant) being 1:0.5 to 1:2.5.

2. The tape preparation according to claim 1, wherein the surfactant comprises at least one selected from the group consisting of sorbitan fatty acid esters and glycerin fatty acid esters.

3. The tape preparation according to claim 1, wherein the surfactant is glycerin fatty acid esters.

4. The tape preparation according to claim 1, wherein the surfactant is at least one selected from the group consisting of glyceryl monooleate, sorbitan monolaurate, and glyceryl monocaprylate.

5. The tape preparation according to claim 1, wherein the surfactant is glyceryl monocaprylate.

6. The tape preparation according to claim 1, wherein the active ingredient is rivastigmine L-tartrate.

7. The tape preparation according to claim 1, wherein a lag time calculated in Hairless Rat Skin Permeability Test is less than or equal to 10 hours.

* * * * *